(12) United States Patent
MacDonald et al.

(10) Patent No.: US 10,912,469 B2
(45) Date of Patent: Feb. 9, 2021

(54) ELECTRONIC FITNESS DEVICE WITH OPTICAL CARDIAC MONITORING

(71) Applicant: Garmin Switzerland GmbH, Schaffhausen (CH)

(72) Inventors: Paul R. MacDonald, Calgary (CA); Christopher J. Kulach, Calgary (CA); James K. Rooney, Cochrane (CA)

(73) Assignee: Garmin Switzerland GmbH

( * ) Notice: Subject to any disclaimer, the term of this patent is extended or adjusted under 35 U.S.C. 154(b) by 452 days.

(21) Appl. No.: 15/860,865

(22) Filed: Jan. 3, 2018

(65) Prior Publication Data

US 2018/0317785 A1 Nov. 8, 2018

Related U.S. Application Data

(60) Provisional application No. 62/501,522, filed on May 4, 2017, provisional application No. 62/571,606, filed (Continued)

(51) Int. Cl.
*A61B 5/1455* (2006.01)
*A61B 5/024* (2006.01)
(Continued)

(52) U.S. Cl.
CPC ...... *A61B 5/02427* (2013.01); *A61B 5/02416* (2013.01); *A61B 5/02438* (2013.01); (Continued)

(58) Field of Classification Search
CPC .............. A61B 5/1455; A61B 5/14551; A61B 5/14552; A61B 5/0205; A61B 5/02427; (Continued)

(56) References Cited

U.S. PATENT DOCUMENTS 5,431,170 A * 7/1995 Mathews ............. A61B 5/0002
600/323
5,524,617 A * 6/1996 Mannheimer ...... A61B 5/14551
356/41
(Continued)

FOREIGN PATENT DOCUMENTS

| EP | 3111834 A1 | 1/2017 |
| WO | 2015116891 A1 | 8/2015 |
| WO | 2017027551 A1 | 2/2017 |

OTHER PUBLICATIONS

Casson et al., Gyroscope vs. accelerometer measurements of motion from wrist PPG, during physical exercise, School of Electrical and Electronic Engineering, The University of Manchester, Manchester, UK, ICT Express 2, 2016, p. 175-179.
(Continued)

*Primary Examiner* — Chu Chuan Liu
(74) *Attorney, Agent, or Firm* — Samuel M. Korte; Max M. Ali

(57) ABSTRACT

An electronic fitness device comprises a first optical transmitter array, a first optical receiver, a second optical receiver, and a processing element. The first optical transmitter array includes first optical transmitter operable to transmit a first optical signal having a first wavelength and a second optical transmitter operable to transmit a second optical signal having a second wavelength. The first optical receiver is operable to receive modulated optical signals and generate a first photoplethysmogram (PPG) signal resulting from the first optical signal and a second PPG signal resulting from the second optical signal. The second optical receiver is operable to receive modulated optical signals and generate a third PPG signal resulting from the first optical signal and a fourth PPG signal resulting from the second optical signal. The processing element is operable to determine cardiac information of the user based on the received PPG signals.

16 Claims, 14 Drawing Sheets

Related U.S. Application Data on Oct. 12, 2017, provisional application No. 62/580,308, filed on Nov. 1, 2017.

(51) Int. Cl.
*A61B 5/00* (2006.01)
*A61B 5/145* (2006.01)

(52) U.S. Cl.
CPC ...... *A61B 5/14535* (2013.01); *A61B 5/14542* (2013.01); *A61B 5/14552* (2013.01); *A61B 5/4875* (2013.01); *A61B 5/681* (2013.01); *A61B 5/6824* (2013.01); *A61B 5/7207* (2013.01); *A61B 5/7246* (2013.01); *A61B 5/7253* (2013.01); *A61B 2503/10* (2013.01); *A61B 2505/09* (2013.01); *A61B 2560/0462* (2013.01); *A61B 2562/0238* (2013.01); *A61B 2562/0242* (2013.01); *A61B 2562/04* (2013.01); *A61B 2562/043* (2013.01)

(58) Field of Classification Search
CPC ... A61B 5/02438; A61B 5/681; A61B 5/7246; A61B 5/7207; A61B 5/7253; A61B 5/4875; A61B 5/02416; A61B 5/6824; A61B 5/14535; A61B 2562/043; A61B 2562/0238; A61B 2562/0242; A61B 2562/04; A61B 5/14532; A61B 5/14546; A61B 5/6826; A61B 5/6816; A61B 5/6829; A61B 5/6838; A61B 2562/00; A61B 2562/046; A61B 2562/06; A61B 2562/063; A61B 2562/066

See application file for complete search history.

(56) References Cited

U.S. PATENT DOCUMENTS

| | | | |
|---|---|---|---|
| 5,632,272 A * | 5/1997 | Diab | A61B 8/5276 600/323 |
| 9,292,008 B1 | 3/2016 | Ahamed et al. | |
| 2003/0109775 A1 * | 6/2003 | O'Neil | A61B 5/14552 600/323 |
| 2011/0060200 A1 | 3/2011 | Bernreuter | |
| 2012/0209095 A1 | 8/2012 | Huiku | |
| 2013/0030267 A1 * | 1/2013 | Lisogurski | A61B 5/14553 600/324 |
| 2014/0213863 A1 | 7/2014 | Loseu et al. | |
| 2015/0065889 A1 | 3/2015 | Gandelman et al. | |
| 2015/0313549 A1 | 11/2015 | Lee et al. | |
| 2016/0287107 A1 | 10/2016 | Szabados et al. | |
| 2016/0296174 A1 | 10/2016 | Isikman et al. | |
| 2018/0317786 A1 | 11/2018 | Kulach et al. | |
| 2018/0317852 A1 | 11/2018 | MacDonald et al. | |

OTHER PUBLICATIONS

Nitzan et al., Pulse oximetry: fundamentals and technology update, Dove Press journal, Medical Devices: Evidence and Research Jul. 8, 2014.

Nogawa et al., Development of an optical arterial hematocrit measurement method: pulse hematometry. Engineering in Medicine and Biology 27th Annual Conference, Sep. 1-4, 2005.

Wieben, O., Light Absorbance in Pulse Oximetry, published prior to Jan. 3, 2018.

Yadhuraj et al., Motion Artifact Reduction in Photoplethysmographic Signals: A Review, International Journal of Innovative Research & Development, Mar. 2013, vol. 2, Issue 3, p. 626-640.

U.S. Appl. No. 15/969,553, Kulach, filed May 2, 2018.

U.S. Appl. No. 15/969,574, MacDonald, filed May 2, 2018.

International Search Report and Written opinion from PCT/EP2018/061445 dated Aug. 16, 2018.

International Search Report and Written Opinion from PCT/EP2018/061446 dated Aug. 16, 2018.

International Search Report and Written Opinion from PCT/EP2019/061444 dated Aug. 16, 2018.

* cited by examiner

ELECTRONIC FITNESS DEVICE WITH OPTICAL CARDIAC MONITORING

RELATED APPLICATIONS

The present application claims the benefit under 35 U.S.C. § 119(e) of U.S. Provisional Application Ser. No. 62/501,522, entitled "Improved SNR of Components in PPG Signal," filed May 4, 2017, Provisional Application Ser. No. 62/571,606, entitled "Improved Optical Cardiac Monitor," filed Oct. 12, 2017, and Provisional Application Ser. No. 62/580,308, entitled "Improved Optical Cardiac Monitor," filed Nov. 1, 2017. The above-referenced Provisional Applications are herein incorporated by reference in their entirety.

BACKGROUND

An electronic fitness device may provide optical cardiac monitoring of a user of the device. The user (wearer) may be any individual who wears the electronic device such that a housing of the electronic device is located proximate to skin of the individual (e.g., worn against the person's wrist, abdomen, leg, etc.). The cardiac monitoring may include physiological metrics and information such as a user's heart rate. The electronic fitness device may utilize a photoplethysmogram (PPG) signal to determine the cardiac monitoring information. The PPG signal is typically output by a photodiode and is commonly utilized to identify changes in the volume of blood in the skin proximate to the photodiode and is collected over a period of time encompassing many heart beats. The electronic fitness device may include optical devices, such as an optical transmitter, which emits an optical signal (light) into the user's skin, and an optical receiver, which receives reflections of the optical signal (light) from the skin and generates a PPG signal corresponding to the intensity of the received light. Typically, the electronic fitness device includes a housing and straps enabling it to be worn on the wrist, arm, leg, or torso, and the optical devices are positioned on the back, or bottom wall, of the housing to orient the optical devices to output and receive light from the user's skin when the device is worn.

SUMMARY

Applicant has observed that the accuracy of the PPG signal may be improved in view of a motion of the user and electronic noise from various sources. Embodiments of the present technology provide an electronic fitness device for determining cardiac monitoring information by utilizing multiple PPG signals in order to reduce or account for the motion and electronic noise.

An embodiment of the electronic fitness device broadly comprises a housing, a first optical transmitter array, a first lens, a first optical receiver, a second lens, a second optical receiver, a third lens, and a processing element. The housing includes a bottom wall and one or more side walls. The first optical transmitter array is positioned in a first opening on the bottom wall and includes a first optical transmitter operable to transmit a first optical signal having a first wavelength and a second optical transmitter operable to transmit a second optical signal having a second wavelength. The first lens covers the first optical transmitter array and is operable to direct the first and second optical signals into the skin of a user. The first optical receiver is positioned in a second opening on the bottom wall at a first distance from the first optical transmitter assembly. The first optical receiver is operable to receive optical signals modulated by the skin of the user and generate a first photoplethysmogram (PPG) signal resulting from the first optical signal and a second PPG signal resulting from the second optical signal. The second lens covers the first optical receiver and is operable to direct optical signals from the skin to the first optical receiver. The second optical receiver is positioned in a third opening on the bottom wall at a second distance from the first optical transmitter array. The second optical receiver is operable to receive optical signals modulated by the skin of the user and generate a third PPG signal resulting from the first optical signal and a fourth PPG signal resulting from the second optical signal. The third lens covers the second optical receiver and is operable to direct optical signals reflected from the skin to the second optical receiver.

The processing element is in electronic communication with the first optical transmitter array and the first and second optical receivers. The processing element is operable to: control the first optical transmitter to transmit the first optical signal during a first period of time, control the second optical transmitter to transmit the second optical signal during a second period of time, receive the PPG signals from the first optical receiver and the second optical receiver, and determine cardiac information of the user based on the received PPG signals.

Another embodiment of the present technology provides an electronic fitness device broadly comprising a housing, a first optical transmitter, a second optical transmitter, a third optical transmitter, a fourth optical transmitter, an optical receiver, and a processing element. The housing includes a bottom wall and one or more side walls. The first optical transmitter is positioned along the bottom wall and is operable to transmit a first optical signal having a first wavelength into the skin of a user. The second optical transmitter is positioned along the bottom wall and is operable to transmit a second optical signal having a second wavelength into the skin of the user. The third optical transmitter is positioned along the bottom wall and is operable to transmit a third optical signal having a third wavelength into the skin of the user. The fourth optical transmitter is positioned along the bottom wall and is operable to transmit a fourth optical signal having a fourth wavelength into the skin of the user. The optical receiver is positioned along the bottom wall. The first optical receiver is operable to receive optical signals modulated by the skin of the user and generate a plurality of wavelength-related photoplethysmogram (PPG) signals, with each wavelength-related PPG signal resulting from a successive one of the optical signals and being related to the wavelength thereof.

The processing element is in electronic communication with the optical transmitters and the optical receiver. The processing element is operable to: control each optical transmitter to transmit its optical signal during a separate period of time, receive the wavelength-related PPG signals from the optical receiver, determine a heart rate of the user based on a first wavelength-related PPG signal, determine a pulse oximetry of the user based on a second and third wavelength-related PPG signal, and utilize a fourth wavelength-related PPG signal to reduce a motion component of any one or more of the first, second, or third wavelength-related PPG signals.

Yet another embodiment of the present technology provides an electronic fitness device broadly comprising a housing, a first optical transmitter, a second optical transmitter, a first optical receiver, a second optical receiver, and a processing element. The housing includes a bottom wall and one or more side walls. The first optical transmitter is positioned along the bottom wall and is operable to transmit a first optical signal having a first wavelength into the skin of a user. The second optical transmitter is positioned along the bottom wall and is operable to transmit a second optical signal having a second wavelength into the skin of the user. The first optical receiver is positioned along the bottom wall. The first optical receiver is operable to receive optical signals modulated by the skin of the user and generate a first photoplethysmogram (PPG) signal related to the first wavelength and a second PPG signal related to the second wavelength. The second optical receiver is positioned along the bottom wall. The second optical receiver is operable to receive optical signals modulated by the skin of the user and generate a third PPG signal related to the first wavelength and a fourth PPG signal related to the second wavelength.

The processing element is in electronic communication with the optical transmitters and the optical receivers. The processing element is operable to: control each optical transmitter to transmit its optical signal during a separate period of time, receive the PPG signals from the first optical receiver and the second optical receiver, utilize the first PPG signal and the third PPG signal to produce a first wavelength PPG signal, utilize the second PPG signal and the fourth PPG signal to produce a second wavelength PPG signal, and determine cardiac information of the user based on the first and second wavelength PPG signals.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present technology will be apparent from the following detailed description of the embodiments and the accompanying drawing figures.

BRIEF DESCRIPTION OF THE DRAWING FIGURES

Embodiments of the present technology are described in detail below with reference to the attached drawing figures, wherein.

Figure 19:
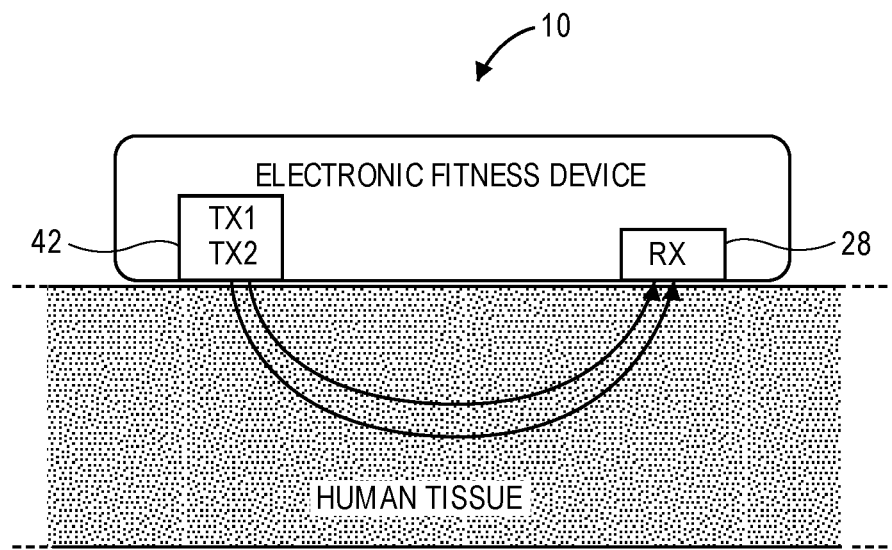
Figure 20:
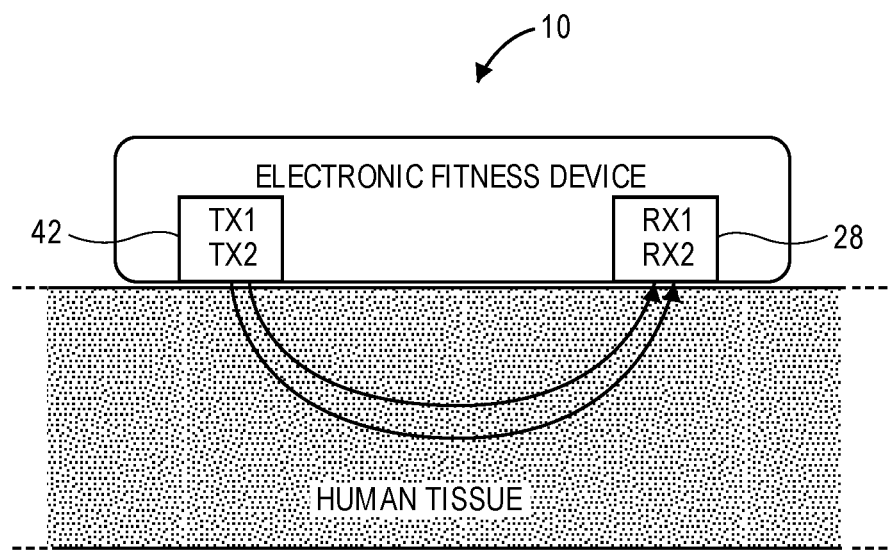

FIG. 19 is a schematic side sectional view of another embodiment of the electronic fitness device while being worn, the electronic fitness device including a first optical transmitter transmitting a first optical signal having a first wavelength and a second optical transmitter transmitting a second optical signal having a second wavelength to one optical receiver; and FIG. 20 is a schematic side sectional view of another embodiment of the electronic fitness device while being worn, the electronic fitness device including a first optical transmitter transmitting a first optical signal having a first wavelength and a second optical transmitter transmitting a second optical signal having a second wavelength to two optical receivers.

The drawing figures do not limit the present technology to the specific embodiments disclosed and described herein. The drawings are not necessarily to scale, emphasis instead being placed upon clearly illustrating the principles of the technology.

DETAILED DESCRIPTION

The following detailed description of the technology references the accompanying drawings that illustrate specific embodiments in which the technology can be practiced. The embodiments are intended to describe aspects of the technology in sufficient detail to enable those skilled in the art to practice the technology. Other embodiments can be utilized and changes can be made without departing from the scope of the present technology. The following detailed description is, therefore, not to be taken in a limiting sense. The scope of the present technology is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
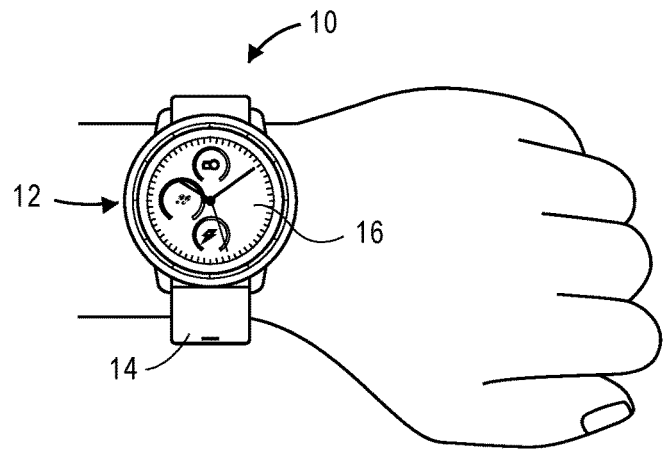
FIG. 1 is a top view of an electronic fitness device, constructed in accordance with various embodiments of the present technology, worn on a user's wrist.
Figure 2:
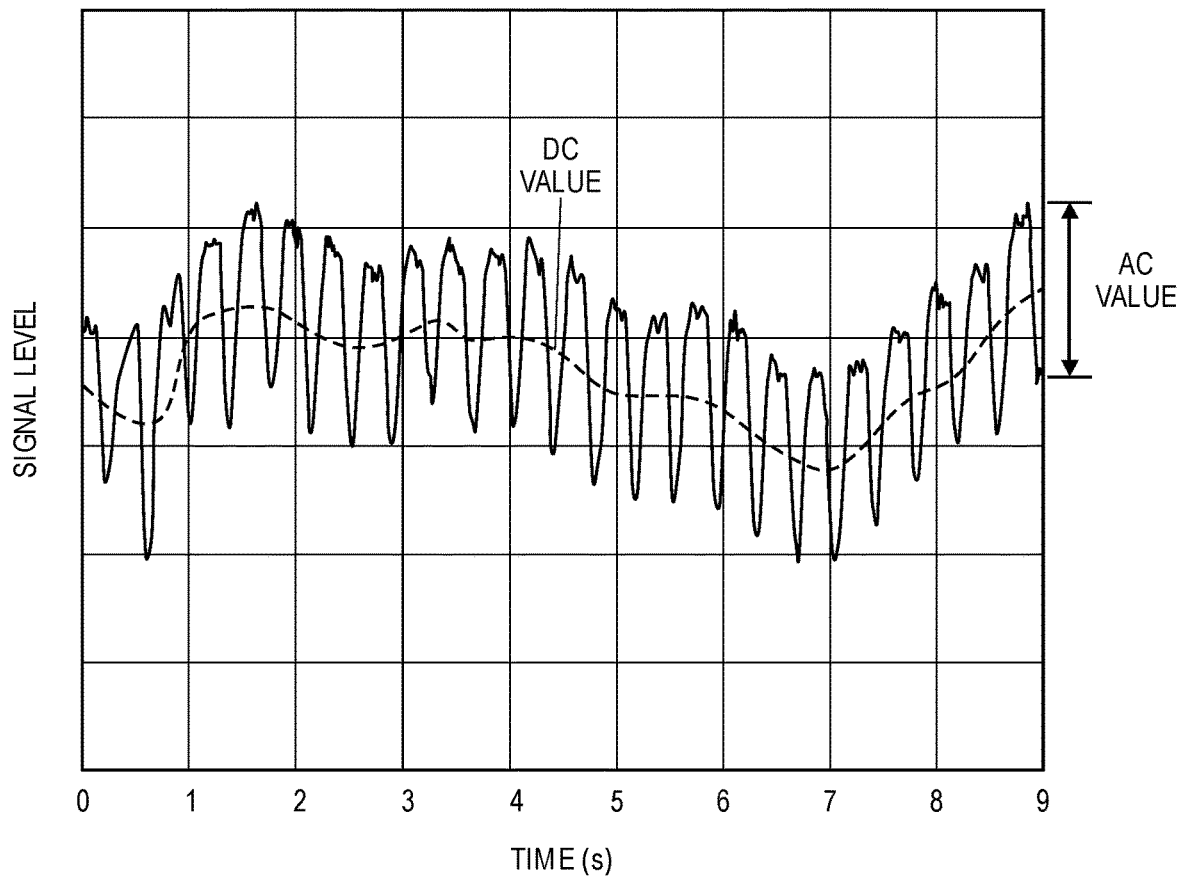
FIG. 2 is a plot of a photoplethysmogram (PPG) signal waveform that may be generated by the electronic fitness device over a period of time.
Figure 3:
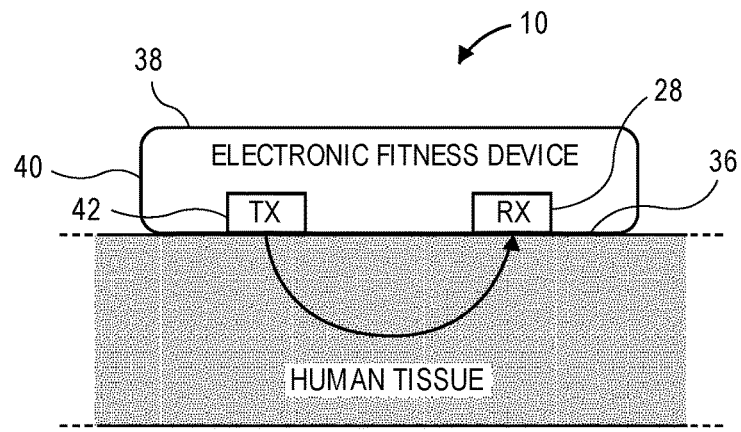
FIG. 3 is a schematic side sectional view of the electronic fitness device and a user's wrist depicting transmission of an optical signal through the skin and tissue of the user.

Embodiments of the present technology provide an electronic fitness device that may be worn on a user's wrist, such as the electronic fitness device shown in FIG. 1, and provides optical cardiac monitoring by generating and utilizing photoplethysmogram (PPG) signals, such as the PPG signal shown as a waveform in FIG. 2. Cardiac monitoring may include determining information such as the user's pulse or heart rate, a pulse oximetry ("Pulse Ox") level (also known as a level of blood oxygen saturation, or SpO2), an estimated stress level, a maximum rate of oxygen consumption (VO2 max), or the like. Referring to FIG. 3, a PPG signal is based on an optical signal (light) emitted from an optical transmitter (TX) into the user's skin (human tissue) proximate to the optical transmitter (TX). The user (wearer) may be any individual who wears the electronic device such that a housing of the electronic device is located proximate to skin of the individual (e.g., worn against the person's wrist, abdomen, leg, etc.). The emitted optical signal penetrates the user's skin to a depth that ranging from tens of microns to several millimeters depending on a variety of criteria, such as the wavelength of transmitted light, presence of blood vessels and composition of the user's skin layers. A portion of the optical signal is reflected, or otherwise transferred, from the skin to an optical receiver (RX), typically a photodiode, that generates the PPG signal. The magnitude of the PPG signal is associated with an intensity of the received optical signal (light). The optical signal may be modulated, or otherwise modified, by the flow of blood through the vessels in the path of the optical signal. Specifically, the optical signal is modulated by the blood flow response to the beating of the user's heart, or the cardiac cycle. Thus, the optical signal received by the optical receiver (RX) has been modulated to include a cardiac component corresponding to the user's cardiac characteristics, which are associated with the user's heartbeat. In turn, the PPG signal generated by the optical receiver (RX) includes the cardiac component corresponding to the user's heartbeat. In addition to the cardiac component, the PPG signal includes undesirable components, such as a motion component resulting from motion of the user, noise components resulting from operation of the device and/or electronic circuitry of the optical receiver (RX), etc.

Generally, as seen in FIG. 2, the PPG signal waveform includes an AC value and a DC value. The AC value of the waveform is a moving peak-to-peak value, i.e., the local maximum minus the local minimum over successive small periods of time. The DC value is the moving average value, i.e., a mean value of the local maximum and the local minimum over successive small periods of time, of the waveform. In some implementations, the DC value is a lowpass-filtered PPG signal. In other implementations, the DC value is a signal formed by connecting and interpolating the local minima or maxima over small periods of time, of the waveform. Still referring to FIG. 2, the cardiac component of the PPG signal is typically a periodic, substantially sinusoidal waveform. A low-frequency AC noise, (e.g. motion component) tends to vary and may be included in the DC value, causing the PPG waveform to move up or down. Motion and various other high-frequency AC noise components tend to pollute the PPG signal and make the identification and extraction of the cardiac signal difficult. Some AC noise components, with frequencies approaching that of the cardiac component modulate the envelope of and/or otherwise distort the cardiac component. Generally, "AC value" corresponds to the cardiac component of the PPG signal. In environments where AC noise is present in the PPG signal, it is desirable to remove the AC noise from the PPG signal before estimating AC value.

A processing element may utilize the PPG to determine a user's heart rate based on a frequency of the cardiac component PPG signal waveform, or simply, the number of cardiac waveform peaks that occur within one minute. In embodiments, the processing element may determine a user's pulse oximetry (blood oxygen level) by utilizing two PPG signals generated by optical signals having different wavelengths—a first PPG signal generated based on a received optical signal transmitted into the skin having a first wavelength and a second PPG signal generated based on a received optical signal transmitted having a second wavelength. The two PPG signals are used to determine an indicator, which is equal to a first quotient of the AC value and the DC value at a first optical signal wavelength divided by a second quotient of the AC value and the DC value at a second optical signal wavelength. The indicator may be given by equation EQ. 1, wherein $\lambda 1$ is the first optical signal wavelength, and $\lambda 2$ is the second optical signal wavelength:

$$\text{Pulse Oximetry Indicator} = \frac{AC_{\lambda 1}/DC_{\lambda 1}}{AC_{\lambda 2}/DC_{\lambda 2}} \qquad [\text{EQ. 1}]$$

The processing element may determine the user's pulse oximetry, or percentage of oxygen in the blood, based on the pulse oximetry indicator and a relationship stored in a memory element that associates the pulse oximetry indicator and a value of the user's pulse oximetry. In embodiments, the relationship may be expressed as a lookup table stored in the memory element that includes a plurality of pulse oximetry indicators and their associated pulse oximetry values for one or more health and/or physiological characteristics. Health characteristics may include age, gender, weight, height and fitness class (i.e., overall physical fitness level). Physiological characteristics may include, but are not limited to, a heartbeat, heart rate, heart-rate variability, speed, distance traveled, calculating calories burned, body temperature, blood pressure, stress intensity level, body energy level, and the like. In embodiments, the processing element may identify a pulse oximetry value based on a determined pulse oximetry indicator (EQ. 1), one or more health characteristics (e.g., age, gender, or weight) and one or more physiological characteristics (e.g., heart rate, blood pressure or heart-rate variability).

As with other calculations determined using signals, accurate determination of the user's heart rate and pulse oximetry value may benefit from reduction of noise components in the PPG signal. For instance, accurate determination of the user's pulse oximetry, particularly the pulse oximetry indicator, may benefit from reduction of noise components and the motion component to enable use of a PPG signal having a signal to noise ratio (SNR) that is maximized and/or a signal to motion noise ratio (SMNR) is maximized.

In embodiments, in order to improve the processing element's ability to accurately obtain the cardiac component (and reduce or remove the undesired components), at least two PPG signals are analyzed simultaneously or nearly simultaneously by the processing element. The two PPG signals result from two optical signals that may each have traveled along different paths, traveled in different orientations, traveled different distances, or so forth, from an optical transmitter to an optical receiver. The resulting PPG signals typically possess different waveform characteristics, such as different overall amplitudes, different noise amplitudes, and different types of noise.

The processing element may receive and analyze the two PPG signals to determine whether a first PPG signal, a second PPG signal, or a combination of the two PPG signals will be utilized to determine the user's heart rate or pulse oximetry. For example, if one of the PPG signals has a low overall amplitude or excessive noise or for other reasons, the higher amplitude and/or less noisy PPG signal (of the two PPG signals) may be selected and the other PPG signal discarded. If the two PPG signals have sufficient amplitude and are not excessively noisy, then both PPG signals may be processed or conditioned.

For instance, the processing element may implement or perform mathematical functions on the PPG signals, such as averaging, correlating, or so forth, which may have the effect of enhancing or maximizing the cardiac component (desired portion) while reducing or minimizing the noise components (undesired portions). In some embodiments, the processing element may compute a moving average (e.g., simple, weighted, etc.) of the two PPG signals to produce a first wavelength PPG signal. In other embodiments, the processing element may correlate the PPG signals by identifying a component of one PPG signal that is substantially correlated with one or more components of the other PPG signal and producing (generating) a PPG signal based on the correlation of the two PPG signals. In embodiments having two pairs of PPG signals, the processing element may identify a component of the first PPG signal that is substantially correlated with one or more components of the third PPG signal, identify a component of the second PPG signal which is substantially correlated with one or more components of the fourth PPG signal, produce a first wavelength PPG signal based on the correlation of the first PPG signal and the third PPG signal, and produce a second wavelength PPG signal based on the correlation of the second PPG signal and the fourth PPG signal. Generally, the cardiac component may be strongly correlated across all PPG signals, whereas the noise components may be weakly correlated. After this preliminary analysis, the processing element may utilize the resulting PPG signal to determine heart rate.

Figure 15:
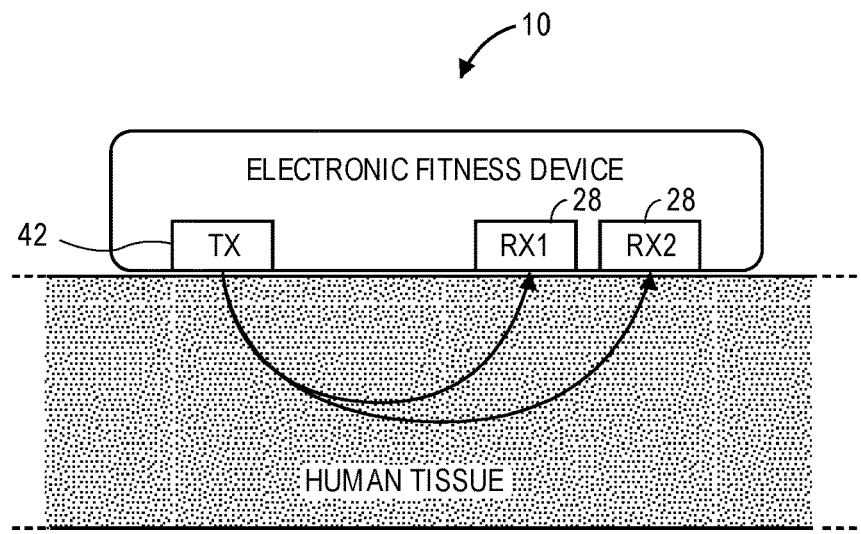
FIG. 15 is a schematic side sectional view of another embodiment of the electronic fitness device while being worn, the electronic fitness device including one optical transmitter transmitting an optical signal to two optical receivers.
Figure 16:
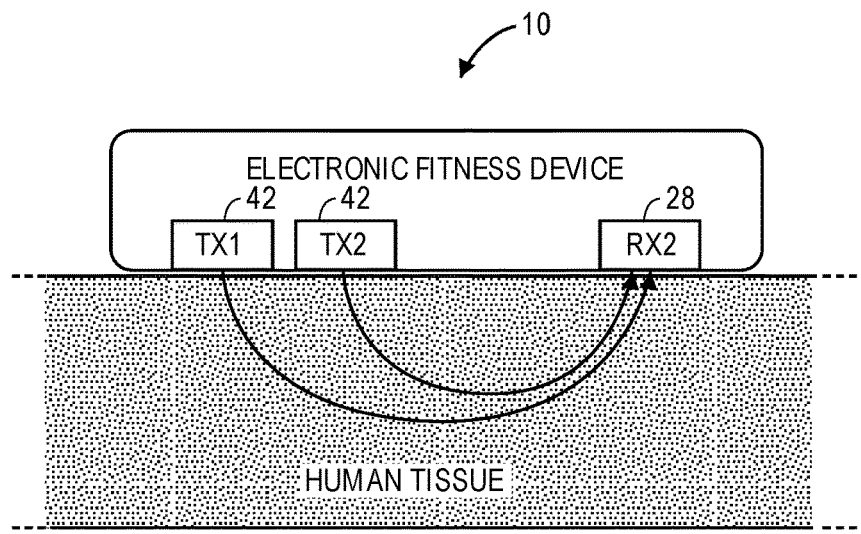
FIG. 16 is a schematic side sectional view of another embodiment of the electronic fitness device while being worn, the electronic fitness device including two optical transmitters with each transmitting an optical signal to one optical receiver.
Figure 17:
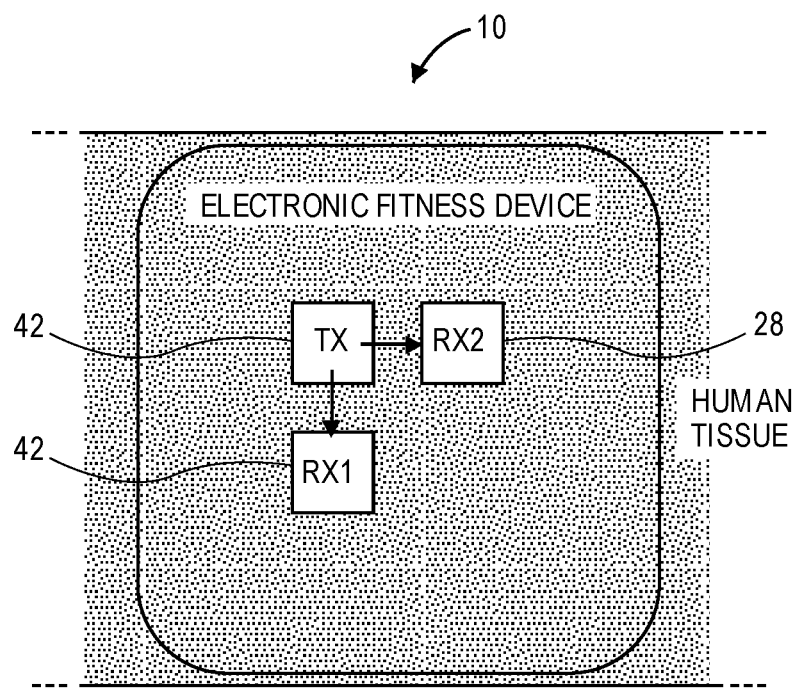
FIG. 17 is a schematic bottom view of another embodiment of the electronic fitness device while being worn, the electronic fitness device including one optical transmitter transmitting an optical signal to two optical receivers.
Figure 18:
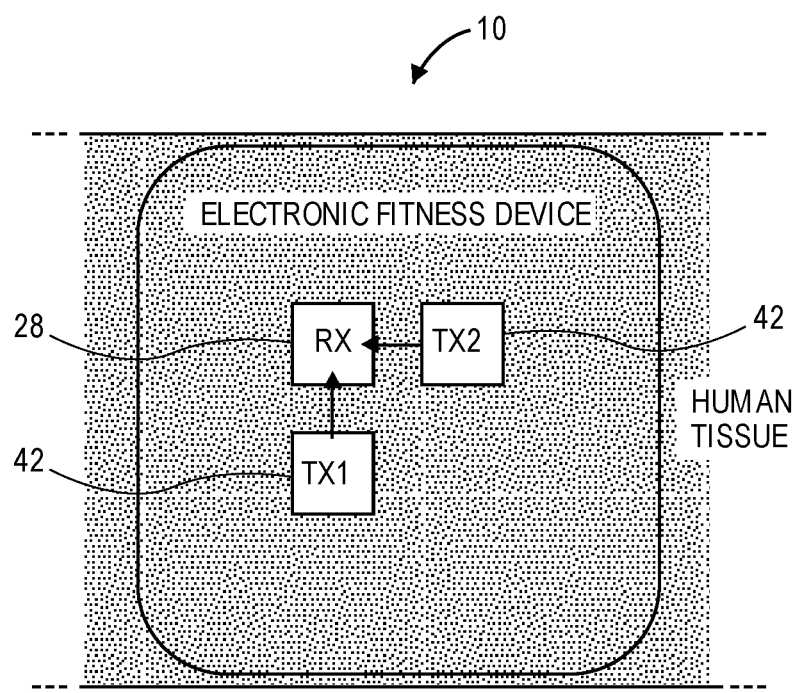
FIG. 18 is a schematic bottom view of another embodiment of the electronic fitness device while being worn, the electronic fitness device including two optical transmitters with each transmitting an optical signal to one optical receiver.

Signal path diversity, which relates to differences in the paths that the optical signals travel, may be achieved or created by use of a plurality of optical transmitters and/or optical receivers. For example, as shown in FIGS. 16, 18 and 19, two optical transmitters may each transmit an optical signal that is received by one optical receiver, such that each optical signal follows a different path, resulting in two differentiated PPG signals. For instance, as shown in FIG. 16, first and second optical transmitters may be positioned at different distances from an optical receiver to produce first and second optical signals which travel different distances, resulting in two differentiated PPG signals. Conversely, as shown in FIGS. 15 and 17, one optical transmitter may transmit an optical signal (across at least two different paths and/or two different path lengths) that is received by two optical receivers, resulting in two differentiated PPG signals. For instance, as shown in FIG. 15, first and second optical receivers may be positioned at different distances from one optical transmitter to produce first and second optical signals which travel different distances, resulting in two differentiated PPG signals. Furthermore, as shown in FIG. 20, multiple optical transmitters may each transmit an optical signal at different wavelengths that is received by multiple optical receivers, resulting in multiple differentiated PPG signals.

In embodiments, to determine pulse oximetry, the processing element may receive and analyze four PPG signals. For example, the PPG signals may be first and second PPG signals resulting from one or more optical signals having a first wavelength and third and fourth PPG signals resulting from one or more optical signals having a second wavelength. The first and second PPG signals may be analyzed by the processing element as discussed above to select or obtain a first wavelength PPG signal, while the third and fourth PPG signals may be analyzed by the processing element to select or obtain a second wavelength PPG signal. The processing element may then utilize the first wavelength PPG signal and the second wavelength PPG signal with EQ. 1 as one of a plurality of steps implemented by the processing element to determine the user's pulse oximetry.

The first and second wavelengths of the optical signal may be produced by two optical transmitters, each optical transmitter configured, operable, or designed, to transmit the optical signal having a particular wavelength. For example, a first optical signal having a first wavelength may be transmitted by a first optical transmitter, and a second optical signal having a second wavelength may be transmitted by a second optical transmitter. As discussed below, for determining a pulse oximetry, the processing element may select a first wavelength in the range of approximately 620 nm to 660 nm and a second wavelength in the range of approximately 850 nm to 940 nm. The two optical signals emitted from the optical transmitters may be received by one or more optical receivers (after the signals have reflected from the user's skin towards the one or more optical receivers).

Figure 4:
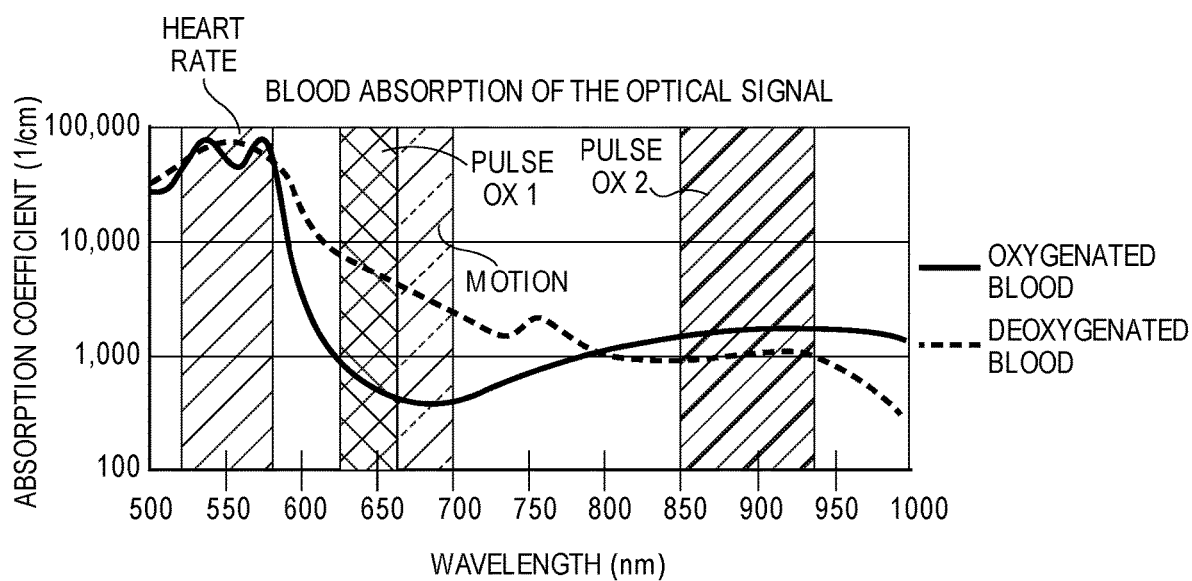
FIG. 4 is a plot of an estimated blood absorption of the optical signal versus a wavelength of the optical signal.
Figure 5:
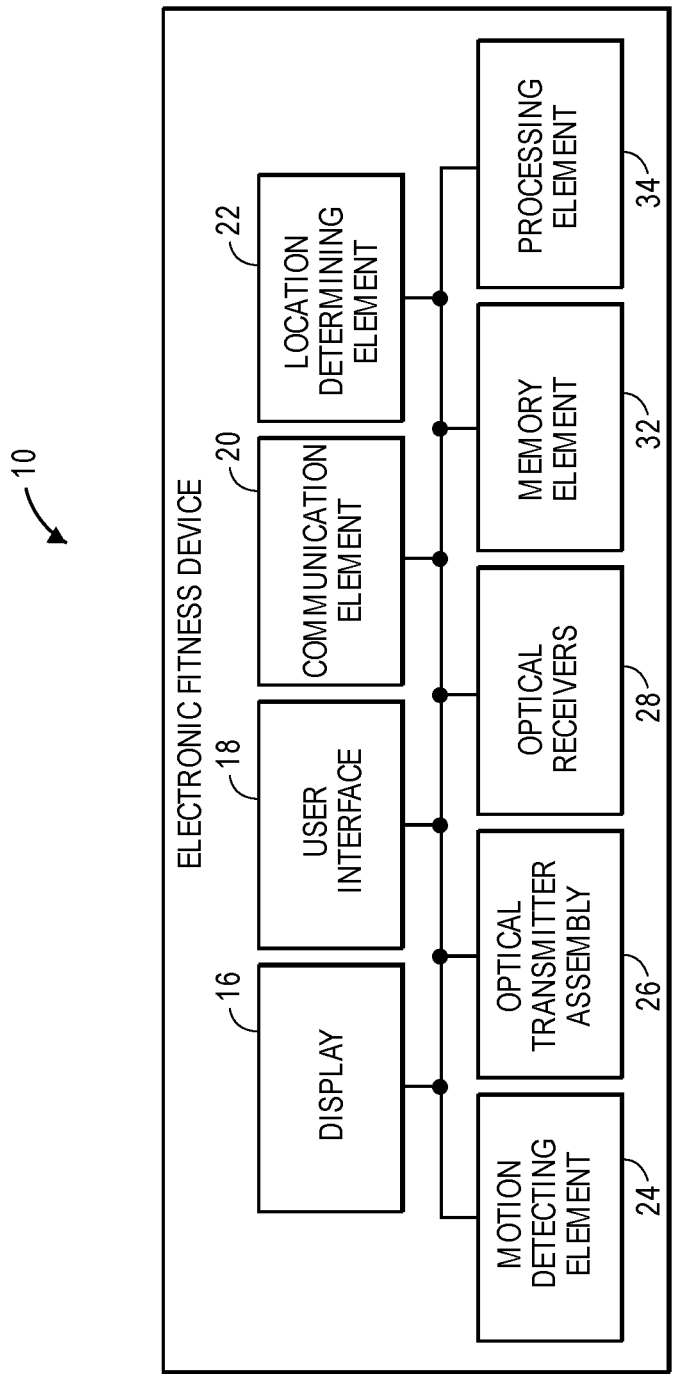
FIG. 5 is a schematic block diagram of various electronic components of the electronic fitness device.

The processing element may cause emitting or transmitting of the optical signal having specific wavelengths for other benefits as well. For instance, it is generally understood that the absorption of the optical signal by a typical user's blood varies according to a wavelength of the optical signal. Furthermore, there are differences in the absorption of optical signal between oxygenated blood and deoxygenated blood. A plot of an absorption coefficient versus optical signal wavelength is shown in FIG. 4 and illustrates the variability of the absorption according to wavelength as well as the differences in absorption between oxygenated blood and deoxygenated blood. The wavelengths at which the absorption coefficient for oxygenated blood absorption of the optical signal is maximized result in a PPG signal with the cardiac component having a greater SNR and/or SMNR—leading to accurate heart rate determination—than other wavelengths. In embodiments, the processing element may cause emission or transmission of an optical signal at a range of wavelengths, among the green and yellow wavelengths of the visible spectrum, labeled in FIG. 4 as "heart rate" the reflections of which may be used by an optical receiver to generate a PPG signal that is utilized by the processing element to determine a user's heart rate.

In embodiments, the processing element may be able to identify a motion component of the PPG signal to reduce or remove the motion component from the PPG signal. The processing element may utilize a signal received from motion detecting electronic devices, such as an accelerometer, to identify motion of the user. The accelerometer may detect motion of the user as well as the environment of the user, such as a car in which the user is traveling. The motion of the car may not contribute significantly to the motion component of the PPG signal. Conversely, tissue motion like ligament motion may affect the PPG signal, but substantially not be detectable by an accelerometer. In other embodiments, the processing element may control an optical transmitter configured to transmit an optical signal having a particular wavelength that is associated with the motion component of the PPG signal and utilize the optical signal to identify and remove the motion component. For example, in embodiments, the processing element may compare the PPG signal resulting from the optical signal being transmitted from a wavelength in the motion range with a PPG signal resulting from the optical signal being transmitted in the heart rate range in a manner discussed above in order to identify and remove (or reduce) the motion component from the PPG signal. As discussed below, a range of wavelengths, among the red wavelengths of the visible spectrum, with which the motion component of the PPG signal is associated is labeled "motion" in FIG. 4.

The choice of wavelengths for the two optical signals resulting in the two PPG signals used to determine the pulse oximetry of the user may improve the accuracy of the pulse oximetry determination. In order to differentiate the response of the optical signal due to the oxygenated blood from the response due to the deoxygenated blood, the processing element may cause optical transmitters to emit or transmit an optical signal for two wavelengths in regions of the plot of FIG. 4 where there is greater separation between the absorption coefficients of the oxygenated blood and the deoxygenated blood. For instance, there is separation between the oxygenated and deoxygenated blood absorption coefficients in the red wavelengths of the visible spectrum and in wavelengths of the lower infrared spectrum. In embodiments, the first wavelength may be a wavelength in a range of red wavelengths, labeled "pulse ox 1" in FIG. 4, and the second wavelength may be a wavelength in a range of infrared wavelengths, labeled "pulse ox 2" in FIG. 4.

Embodiments of the present technology will now be described in more detail with reference to the drawing figures. Referring initially to FIGS. 1, 3, 5-7, and 11, an electronic fitness device 10 for providing optical cardiac monitoring is illustrated. An exemplary electronic fitness device 10 may be embodied by a smart watch or a fitness band that is typically worn on a user's wrist, but may also be embodied by bands or belts worn on the user's arm, leg, or torso. Other examples of the electronic fitness device 10 may include smartphones, personal data assistants, or the like which include a surface, operable to retain optical devices, that can be pressed against the user's skin. The electronic fitness device 10 may broadly comprise a housing 12, a wrist band 14, a display 16, a user interface 18, a communication element 20, a location determining element 22, a motion detecting element 24, an optical transmitter array(s) 26, an optical receiver(s) 28, a lens(es) 30, a memory element 32, and a processing element 34.

The housing 12 generally houses or retains other components of the electronic fitness device 10 and may include or be coupled to the wrist band 14. As seen in FIG. 3, the housing 12 may include a bottom wall 36, an upper surface 38, and at least one side wall 40 that bound an internal cavity (not shown in the figures). The bottom wall 36 may include a lower, outer surface that contacts the user's wrist while the user is wearing the electronic fitness device 10. The upper surface 38 opposes the bottom wall 36. In various embodiments, the upper surface 38 may further include an opening that extends from the upper surface to the internal cavity. In some embodiments, such as the exemplary embodiments shown in the figures, the bottom wall 36 of the housing 12 may have a round, circular, or oval shape, with a single circumferential side wall 40. In other embodiments, the bottom wall 36 may have a four-sided shape, such as a square or rectangle, or other polygonal shape, with the housing 12 including four or more sidewalls. The bottom wall 36 includes one or more openings through which one or more optical transmitter array(s) 26 emit or transmit an optical signal and one or more optical receiver(s) 28 receive reflections of the optical signal from the user's skin. The one or more openings within the bottom wall 36 may be covered by one or more lenses 30 through which the optical signal may be transmitted and received.

The display 16 generally presents the information mentioned above, such as time of day, current location, and the like. The display 16 may be implemented in one of the following technologies: light-emitting diode (LED), organic LED (OLED), Light Emitting Polymer (LEP) or Polymer LED (PLED), liquid crystal display (LCD), thin film transistor (TFT) LCD, LED side-lit or back-lit LCD, or the like, or combinations thereof. In some embodiments, the display 16 may have a round, circular, or oval shape. In other embodiments, the display 16 may possess a square or a rectangular aspect ratio which may be viewed in either a landscape or a portrait orientation.

The user interface 18 generally allows the user to directly interact with the electronic fitness device 10 and may include pushbuttons, rotating knobs, or the like. In various embodiments, the display 16 may also include a touch screen occupying the entire display 16 or a portion thereof so that the display 16 functions as at least a portion of the user interface 18. The touch screen may allow the user to interact with the electronic fitness device 10 by physically touching, swiping, or gesturing on areas of the display 16.

The communication element 20 generally allows communication with external systems or devices. The communication element 20 may include signal and/or data transmitting and receiving circuits, such as antennas, amplifiers, filters, mixers, oscillators, digital signal processors (DSPs), and the like. The communication element 20 may establish communication wirelessly by utilizing radio frequency (RF) signals and/or data that comply with communication standards such as cellular 2G, 3G, 4G, LTE, or 5G, Institute of Electrical and Electronics Engineers (IEEE) 802.11 standard such as Wi-Fi, IEEE 802.16 standard such as WiMAX, Bluetooth™, or combinations thereof. In addition, the communication element 20 may utilize communication standards such as ANT, ANT+, Bluetooth™ low energy (BLE), the industrial, scientific, and medical (ISM) band at 2.4 gigahertz (GHz), or the like. Alternatively, or in addition, the communication element 20 may establish communication through connectors or couplers that receive metal conductor wires or cables which are compatible with networking technologies such as Ethernet. In certain embodiments, the communication element 20 may also couple with optical fiber cables. The communication element 20 may be in electronic communication with the memory element 32 and the processing element 34.

The location determining element 22 generally determines a current geolocation of the electronic fitness device 10 and may receive and process radio frequency (RF) signals from a global navigation satellite system (GNSS) such as the global positioning system (GPS) primarily used in the United States, the GLONASS system primarily used in the Soviet Union, or the Galileo system primarily used in Europe. The location determining element 22 may accompany or include an antenna to assist in receiving the satellite signals. The antenna may be a patch antenna, a linear antenna, or any other type of antenna that can be used with location or navigation devices. The location determining element 22 may include satellite navigation receivers, processors, controllers, other computing devices, or combinations thereof, and memory. The location determining element 22 may process a signal, referred to herein as a "location signal", from one or more satellites that includes data from which geographic information such as the current geolocation is derived. The current geolocation may include coordinates, such as the latitude and longitude, of the current location of the electronic fitness device 10. The location determining element 22 may communicate the current geolocation to the processing element 34, the memory element 32, or both.

Although embodiments of the location determining element 22 may include a satellite navigation receiver, it will be appreciated that other location-determining technology may be used. For example, cellular towers or any customized transmitting radio frequency towers can be used instead of satellites may be used to determine the location of the electronic fitness device 10 by receiving data from at least three transmitting locations and then performing basic triangulation calculations to determine the relative position of the device with respect to the transmitting locations. With such a configuration, any standard geometric triangulation algorithm can be used to determine the location of the electronic fitness device 10. The location determining element 22 may also include or be coupled with a pedometer, accelerometer, compass, or other dead-reckoning components which allow it to determine the location of the device 10. The location determining element 22 may determine the current geographic location through a communications network, such as by using Assisted GPS (A-GPS), or from another electronic fitness device. The location determining element 22 may even receive location data directly from a user.

The motion detecting element 24 generally detects movement of the electronic fitness device 10 and may include accelerometers, tilt sensors, inclinometers, gyroscopes, combinations thereof, or other devices including piezoelectric, piezoresistive, capacitive sensing, or micro electromechanical systems (MEMS) components. The motion detecting element 24 may sense motion along one axis of motion or multiple axes of motion. Motion detecting element 24 may sense motion along three orthogonal axes, such as X, Y, and Z. In various embodiments, the motion detecting element 24 may measure the acceleration, such as acceleration due to the gravitation (G) force, of the user and may output the measured data in a motion signal having a digital binary format.

In embodiments, the optical transmitter array(s) 26 include a first optical transmitter array 26A and a second optical transmitter array 26B. Each optical transmitter array 26 includes a plurality of optical transmitters 42 (each optical transmitter 42 indicated in FIGS. 6 and 7 with a "TX" prefix). In some embodiments, each optical transmitter 42 may include a photonic generator, such as a light-emitting diode (LED), a modulator, a top emitter, an edge emitter, or the like. The photonic generator receives an electrical input signal from the processing element 34 that may be a control signal, such as an electric voltage or electric current that is analog or digital, or data, either of which is indicative of activating or energizing the optical transmitter 42 to transmit (emit) an optical signal having a desired amplitude, frequency, and duration. The photonic generator of each optical transmitter 42 transmits electromagnetic radiation having a particular wavelength (the optical signal) in the visible light spectrum, which is typically between approximately 400 nanometers (nm) to 700 nm, or in the infrared spectrum, which is typically between approximately 700 nm to 1 millimeter (mm). However, in some embodiments, the photonic generator transmits electromagnetic radiation in wavelength range of 1000 nm to 1500 nm. The wavelength of the optical signal is generally determined by, or varies according to, the material from which the photonic generator of each optical transmitter 42 is formed. The optical signal may comprise a sequence of pulses, a periodic or non-periodic waveform, a constant level for a given period of time, or the like, or combinations thereof. In other embodiments, each optical transmitter 42 may include a driver circuit, with electronic circuitry such as amplifier and an optional filter, electrically coupled to the photonic generator. The driver circuit may receive the electrical input signal (control signal) from the processing element 34 and the driver circuit may generate an electric voltage or electric current to the photonic generator, which in turn, transmits (emits) the optical signal.

Figure 7:
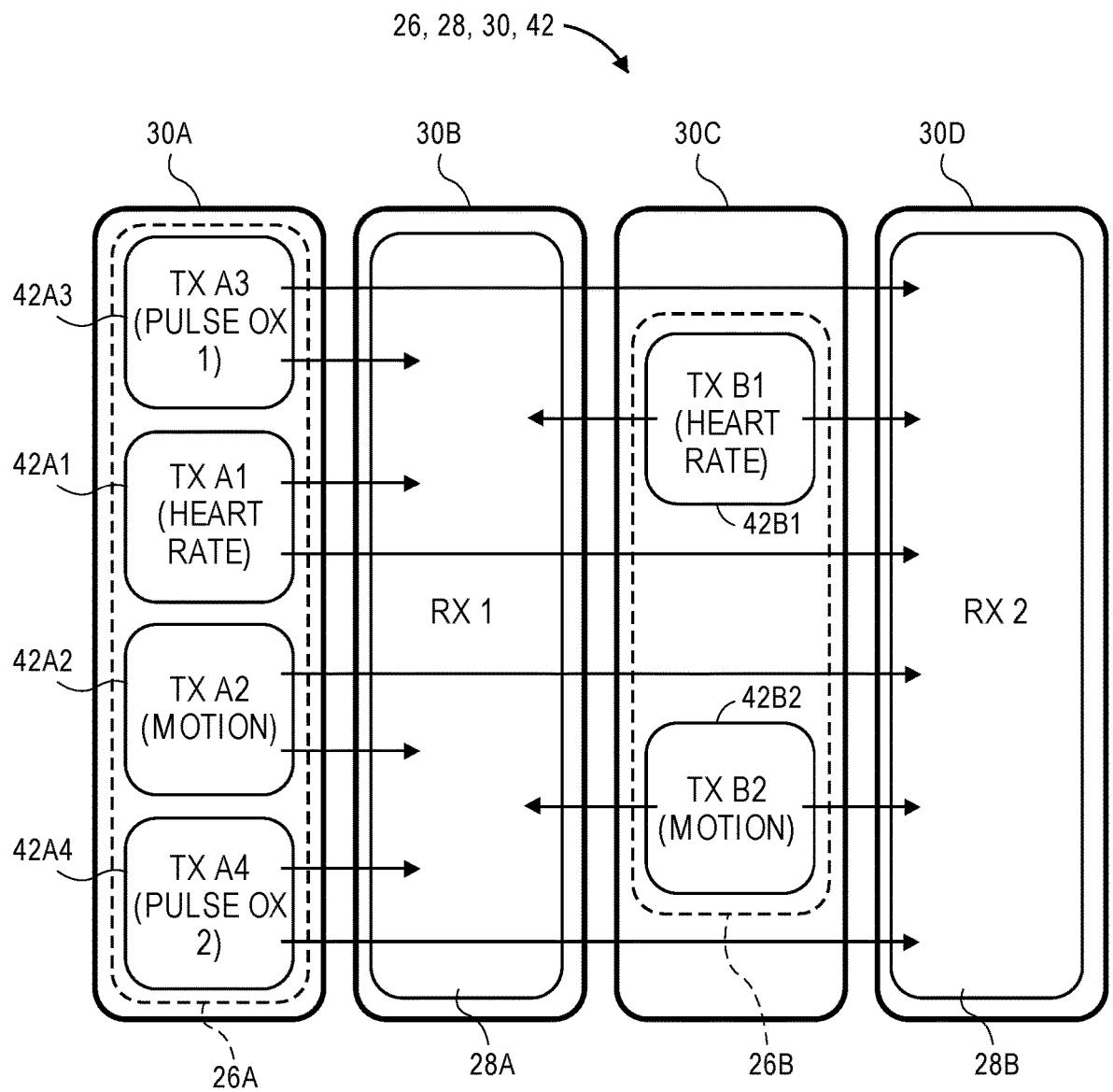
FIG. 7 is another schematic of the optical transmitters and optical receivers of FIG. 6, the optical transmitters configured to output optical signals utilized to implement the indicated functions based on the optical signals received by the optical receivers.

The first optical transmitter array 26A may include four optical transmitters 42: a first optical transmitter 42A1 configured or operable to transmit an optical signal having a first wavelength ($\lambda 1$), a second optical transmitter 42A2 configured or operable to transmit an optical signal having a second wavelength ($\lambda 2$), a third optical transmitter 42A3 configured or operable to transmit an optical signal having a third wavelength ($\lambda 3$), and a fourth optical transmitter 42A4 configured or operable to transmit an optical signal having a fourth wavelength ($\lambda 4$). In various embodiments, the processing element 34 may utilize each wavelength to perform a certain function, as shown in FIG. 7, using a PPG signal generated by one or more optical receiver(s) 28 that receive reflections of each optical signal from the user's skin.

In an exemplary embodiment, the processing element 34 may output a control signal to: an optical transmitter configured to transmit an optical signal having the first wavelength the reflection of which provides a PPG signal to the processing element 34 enabling an accurate determination of the user's heart rate in the range from approximately 520 nm to approximately 580 nm; an optical transmitter configured to transmit an optical signal having the second wavelength, the reflection of which amplifies the motion component of the PPG signal relative to the cardiac component to enable isolation of the motion component, in the range from approximately 660 nm to approximately 700 nm; an optical transmitter configured to transmit an optical signal having the third wavelength, the reflection of which provides a first PPG signal to the processing element 34 for use with determining a pulse oximetry in the red range of the spectrum from approximately 620 nm to approximately 660 nm; and an optical transmitter configured to transmit an optical signal having the fourth wavelength, the reflection of which provides a second PPG signal to the processing element 34 for use with determining a pulse oximetry in the infrared range of the spectrum from approximately 850 nm to approximately 940 nm. In embodiments, specific exemplary wavelengths may include approximately 540 nm for the first wavelength, approximately 680 nm for the second wavelength, approximately 660 nm for the third wavelength, and approximately 940 nm for the fourth wavelength.

Each optical transmitter 42 of the first optical transmitter array 26A may be integrated on a single substrate, such as a printed circuit board, or may be positioned in close proximity to one another. Generally, the optical transmitters 42 are oriented or located to form a linear array, as shown in FIG. 7, although the relative positioning of each optical transmitter 42 within the array maybe rearranged and still remain within the scope of the present technology. The first optical transmitter array 26A is positioned in an opening on the bottom wall 36 of the housing 12 and may be positioned under a lens 30. In some embodiments, each optical transmitter 42 may be positioned in its own opening of the bottom wall 36.

The second optical transmitter array 26B may include two optical transmitters 42: a first optical transmitter 42B1 configured or operable to transmit an optical signal having a fifth wavelength ($\lambda 5$) and a second optical transmitter 42B2 configured or operable to transmit an optical signal having a sixth wavelength ($\lambda 6$). Similar to the first optical transmitter array 26A, the processing element 34 may utilize wavelengths of the second optical transmitter array 26B to perform a certain function, as shown in FIG. 7, using a PPG signal generated by one or more optical receiver(s) 28 that receive reflections of each optical signal from the user's skin. In an exemplary embodiment, the processing element 34 may output a control signal to: an optical transmitter configured to transmit an optical signal having the fifth wavelength, the reflection of which provides a PPG signal to the processing element 34 enabling an accurate determination of the user's heart rate in the range from approximately 520 nm to approximately 580 nm; and an optical transmitter configured to transmit an optical signal having the sixth wavelength, the reflection of which provides a PPG signal to the processing element 34 enabling isolation of the motion component of the PPG signal in the range from approximately 660 nm to approximately 700 nm.

In some embodiments, the first wavelength and the fifth wavelength may be substantially equal. Similarly, the second wavelength and the sixth wavelength may be substantially equal. Therefore, the wavelengths of one or more optical transmitters 42 of the second optical transmitter array 26B may duplicate some of the functionality of one or more optical transmitters 42 of the first optical transmitter array 26A, but given that the optical signals transmitted from the second optical transmitter array 26B follow a different path in comparison to the optical signals transmitted from the first optical transmitter array 26A, there is signal path differentiation or diversity between the optical signals. As detailed herein, the processing element 34 may utilize the plurality of optical signals, which provide signal path diversity, to more accurately determine the user's heart rate and/or pulse oximetry.

Each of optical transmitters 42 of the second optical transmitter array 26B may be integrated on a single substrate, such as a printed circuit board, or may be positioned in close proximity to one another. The second optical transmitter array 26B is positioned in an opening on the bottom wall 36 of the housing 12 and may be positioned under a lens 30. In some embodiments, each optical transmitter 42 may be positioned in its own opening of the bottom wall 36. At any rate, the second optical transmitter array 26B is separated from the first optical transmitter array 26A by a first distance. In various embodiments, the longitudinal axis line (through the center of each optical transmitter 42) of the first optical transmitter array 26A is parallel to the longitudinal axis line of the second optical transmitter array 26B.

Figure 6:
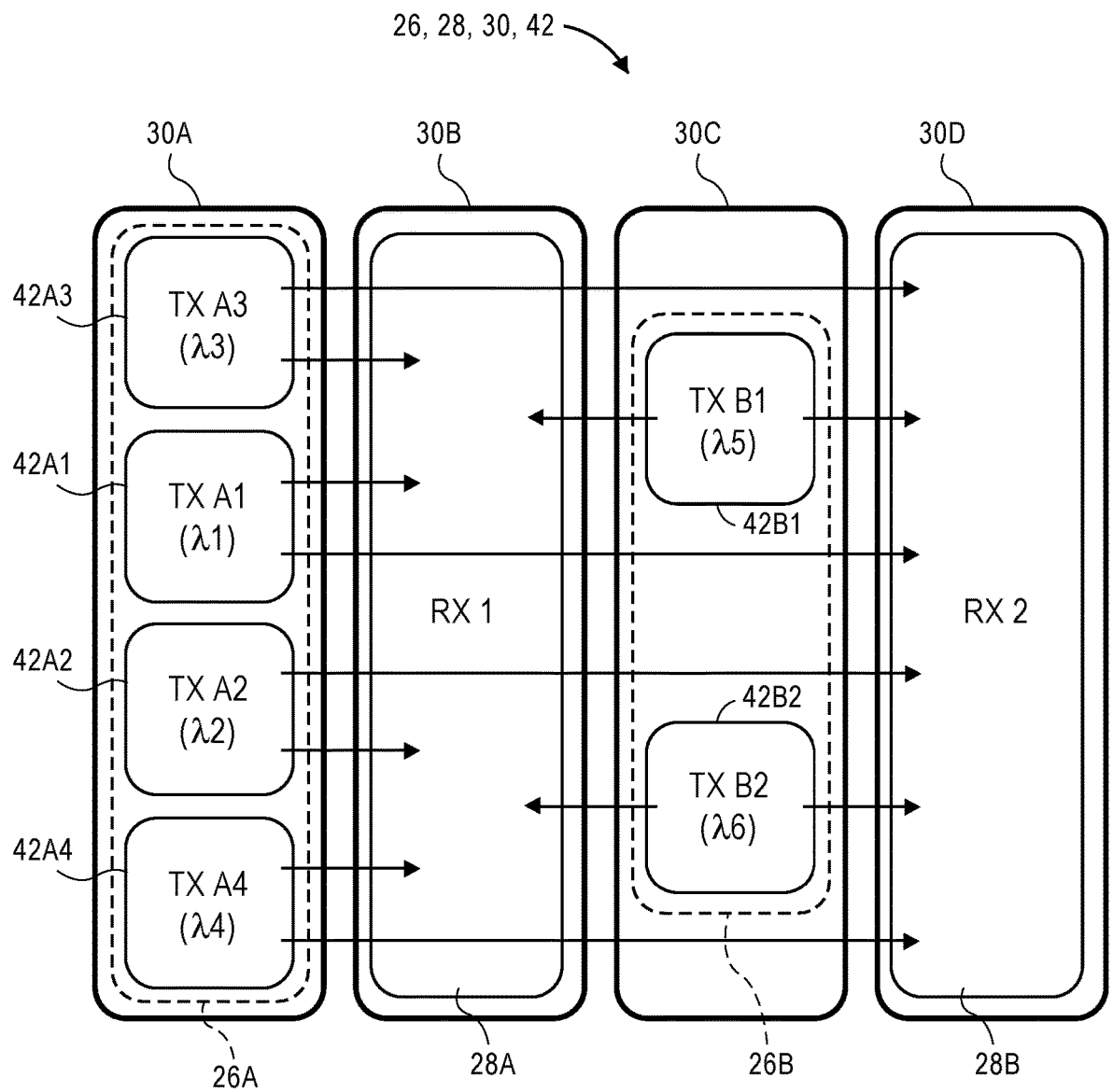
FIG. 6 is a schematic view of a plurality of optical transmitter arrays and optical receivers illustrating pathways of the optical signal transmitted by each of the optical transmitters and received by a plurality of optical receivers.

The electronic fitness device 10 may include a first optical receiver 28A and a second optical receiver 28B (each optical receiver 28 indicated in FIGS. 6 and 7 with the "RX" prefix). In some embodiments, each optical receiver 28 may include a photodetector, such as a photodiode, a phototransistor, a photoresistor, a phototube, or the like. The photodetector receives electromagnetic radiation having multiple wavelengths (typically any of the wavelengths generated by the photonic generators) and in response, generates a PPG signal, comprising an electric current, an electric voltage, or other electrical parameter, that corresponds to the intensity of the modulated optical signal in amplitude and frequency that is transmitted by an optical transmitter 42 and reflected from the user's skin. Given that the optical receivers 28 may receive multiple optical signals, each having a particular wavelength, each PPG signal generated by either optical receiver 28 may be a particular wavelength-related PPG signal because it includes characteristics or components resulting from, or related to, the particular wavelength of the optical signal transmitted (emitted) by an optical transmitter 42 of the first or second optical transmitter arrays 26A, 26B. In other embodiments, each optical receiver 28 may include the photodetector electrically coupled to an amplifier circuit followed by an analog-to-digital converter (ADC). The photodetector may receive electromagnetic radiation having multiple wavelengths and in response, may generate an output signal, comprising an electric current, an electric voltage, or other electrical parameter that corresponds to the intensity of the modulated optical signal in amplitude and frequency that is transmitted by an optical transmitter 42 and reflected from the user's skin. The amplifier circuit may receive the output signal from the photodetector and amplify it to produce an amplified output signal that is analog and communicated to the ADC. The ADC may sample the amplified output signal and output a PPG signal, which is converted into a corresponding stream of digital data.

Each optical receiver 28 may generate a plurality of PPG signals, each PPG signal resulting from an optical signal transmitted by one of the optical transmitters 42 of the first or second optical transmitter arrays 26A, 26B. In embodiments having a plurality of optical receivers 28, for example, the first optical receiver 28A may generate a first PPG signal resulting from the optical signal received from the first optical transmitter 42, a second PPG signal resulting from the optical signal received from the second optical transmitter 42, and so forth. Likewise, the second optical receiver 28B may generate a first PPG signal resulting from the optical signal received from the first optical transmitter 42, a second PPG signal resulting from the optical signal received from the second optical transmitter 42, and so forth. Alternatively, the first optical receiver 28A may generate a first PPG signal resulting from the optical signal received from the first optical transmitter 42, while the second optical receiver 28B may generate a second PPG signal resulting from the optical signal received from the first optical transmitter 42, and so forth.

The optical receiver 28 is typically a photodiode and may be any other device configured to generate a PPG signal based on the intensity of light received by a sensor element. The first optical receiver 28A is positioned in an opening on the bottom wall 36 of the housing 12 between the first optical transmitter array 26A and the second optical transmitter array 26B, while the second optical receiver 28B may be positioned in an opening on the bottom wall 36 on the opposing side of either the second optical transmitter array 26B (as shown in FIGS. 6 and 7) or the first optical transmitter array 26A (not shown).

In some implementations, the housing 12 and wrist band 14 may be positioned such that the optical components (optical transmitter array(s) 26 and optical receiver(s) 28) are positioned substantially over (i.e. most proximally to) one of the user's wrist bones. For example, the optical components may be positioned substantially over the ulna bone or substantially over the radius bone.

The electronic fitness device 10 may include a first lens 30A, a second lens 30B, a third lens 30C, and a fourth lens 30D. One or more openings within the bottom wall 36 may be covered by the first lens 30A, the second lens 30B, the third lens 30C, and the fourth lens 30D such that the optical signals may be transmitted and received through each lens 30. The lenses 30 generally provide cover for the optical transmitters 42 and the optical receivers 28. In addition, the lenses 30 may be configured, operable, shaped, or formed to provide focusing, collimation, refraction, diffraction, and so forth. Furthermore, some lenses 30, such as the lenses 30 that cover the optical transmitters 42, may provide some functions, while other lenses 30, such as the lenses 30 that cover the optical receivers 28, may provide other functions. The lenses 30 that cover the optical transmitters 42 may direct optical signals transmitted by the optical transmitters 42 to the skin of the user. The lenses 30 that cover the optical receivers 28 may direct the optical signals reflected from the skin to the optical receivers 28. The lenses 30 may be constructed from glass, polymers, or the like. The first lens 30A may cover the first optical transmitter array 26A, the second lens 30B may cover the first receiver 28A, the third lens 30C may cover the second optical receiver 28B, and the fourth lens 30D may cover the second optical transmitter array 26B. In various embodiments, all of the lenses 30 may be the same size and shape and may be aligned with one another on the bottom wall 36. In addition, one surface of each lens 30 may be coupled to an outer surface of the bottom wall 36 of the housing 12.

The memory element 32 may be embodied by devices or components that store data in general, and digital or binary data in particular, and may include exemplary electronic hardware data storage devices or components such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory element 32 may be embedded in, or packaged in the same package as, the processing element 34. The memory element 32 may include, or may constitute, a "computer-readable medium". The memory element 32 may store the instructions, code, code statements, code segments, software, firmware, programs, applications, apps, services, daemons, or the like that are executed by the processing element 34. The memory element 32 may also store settings, data, documents, sound files, photographs, movies, images, databases, and the like.

The processing element 34 may include electronic hardware components such as processors, microprocessors (single-core or multi-core), microcontrollers, digital signal processors (DSPs), field-programmable gate arrays (FPGAs), analog and/or digital application-specific integrated circuits (ASICs), or the like, or combinations thereof. In some embodiments, the processing element 34 may also include ADC circuitry. The processing element 34 may generally execute, process, or run instructions, code, code segments, code statements, software, firmware, programs, applications, apps, processes, services, daemons, or the like. The processing element 34 may also include hardware components such as finite-state machines, sequential and combinational logic, and other electronic circuits that can perform the functions necessary for the operation of the current invention. The processing element 34 may be in electronic communication with the other electronic components through serial or parallel links that include universal busses, address busses, data busses, control lines, and the like. Furthermore, the processing element 34 may include multiple physically separated but logically and electronically connected functional blocks.

The processing element 34 may be operable, configured, or programmed to perform the following functions through hardware, software, firmware, or combinations thereof. The processing element 34 generates the electrical input signal or control signal, which may include an electric voltage or electric current that is constant or variable, analog or digital, or data, as a single number or a stream of numbers, and communicates the signal to the optical transmitter 42 in order to control operation of each optical transmitter 42 within the optical transmitter array(s) 26. The processing element 34 is operable to communicate the electrical input signal or control signal to each optical transmitter 42 individually at different times, to one or more groups of the optical transmitters 42 simultaneously, or to all of the optical transmitters 42 simultaneously. Thus, the processing element 34 may generate and transmit six electrical input signals or control signals, one for each optical transmitter 42.

The processing element 34 may be configured to control a plurality of optical transmitters 42 within each optical transmitter array 26. The processing element 34 generates the electrical input signal or control signal and communicates it to a first one of the optical transmitters 42 (depending on the requested data—heart rate or pulse oximetry) for a first time period, ranging from several microseconds to approximately 1 minute. The processing element 34 may generate the electrical input signal or control signal and communicate it to a second one of the optical transmitters 42 for a second time period, or it may wait a short time period or interval before generating the electrical input signal or control signal and communicating it to the second one of the optical transmitters 42 for the second time period. Either way, the first time period and the second time period do not overlap and correspond to different moments of time. It is to be understood that a duration of the first time period and a duration of the second time period may be different or substantially equal. In various embodiments, the processing element 34 may continue generating and communicating the electrical input signal or control signal for each optical transmitter 42 in alternating time periods, such that the processing element 34 generates and communicates the electrical input signal to the first one of the optical transmitters 42 during odd-numbered time periods, and the processing element 34 generates and communicates the electrical input signal to the second one of the optical transmitters 42 during even-numbered time periods. If the processing element 34 needs to utilize three or more optical transmitters 42, then the processing element 34 generates and communicates the electrical input signal or control signal to each optical transmitter 42 in a successive time period such that the processing element 34 may repeat the process by generating and communicating the electrical input signal or control signal to the first of the optical transmitters 42 after the last of the optical transmitters 42 within the optical transmitter array 26. It is to be understood that the processing element 34 may be similarly configured to simultaneously control a plurality of optical transmitters 42 within additional optical transmitter array(s) 26.

Generating the electrical input signal or control signal in this time division multiplexing (TDM) fashion allows the processing element 34 to distinguish the PPG signals resulting from optical signals having different wavelengths when transmitted (emitted) by an optical transmitter 42 within an optical transmitter array 26. Given that the optical receivers 28 respond to broadband electromagnetic radiation, each optical receiver 28 can receive two or more optical signals having two or more wavelengths. However, each optical receiver 28 generates only one PPG signal at each moment of time (at any instant). The processing element 34 may cause the optical signal transmitted by each optical transmitter 42 (from the first optical transmitter array 26A and the second optical transmitter array 26B) to be transmitted at a predetermined time. For instance, the processing element 34 may cause the first optical transmitter 42A1 (TX A1—Heart Rate) of the first optical transmitter array 26A and the first optical transmitter 42B1 (TX B1—Heart Rate) of the second optical transmitter array 26B to both simultaneously transmit an optical signal during the same or an overlapping time period. Similarly, the processing element 34 may cause the first optical transmitter 42A1 (TX A1—Heart Rate) and the second optical transmitter 42A2 (TX A2—Motion) of the first optical transmitter array 26A and the first optical transmitter 42B1 (TX B1—Heart Rate) and the second optical transmitter 42A2 (TX B2—Motion) of the second optical transmitter array 26B to all simultaneously transmit an optical signal during the same or an overlapping time period. Alternatively, the processing element 34 may cause the first optical transmitter 42A1 (TX A1—Heart Rate) and the first optical transmitter 42B1 (TX B1—Heart Rate) of the first and second optical transmitter arrays 26A and 26B, respectively, to each transmit an optical signal during a first time period and the processing element 34 may cause the second optical transmitter 42A2 (TX A2—Motion) and the second optical transmitter 42B2 (TX B2—Motion) of the first and second optical transmitter arrays 26A and 26B, respectively, to each transmit an optical signal during a second time period such that the first and second time periods do not overlap (i.e., the optical transmitters 42A1, 42B1 may transmit optical signals before the optical transmitters 42A2, 42B2 in a repetitive manner). In some embodiments, the processing element 34 may cause each of the first optical transmitter 42A1 (TX A1—Heart Rate) and the second optical transmitter 42A2 (TX A2—Motion) of the first optical transmitter array 26A and the first optical transmitter 42B1 (TX B1—Heart Rate) and the second optical transmitter 42A2 (TX B2—Motion) of the second optical transmitter array 26B to sequentially transmit an optical signal during a first time period, a second time period, a third time period, and a fourth time period, respectively, such that only one of the four optical transmitters 42 is transmitting an optical signal at a moment of time (at any instant). In addition, multiple optical transmitters 42 each transmitting an optical signal simultaneously may saturate the photodetector of the optical receiver 28 with their combined electromagnetic radiation, resulting in a PPG signal that is not useful for determining a user's cardiac information, such as heart rate or pulse oximetry.

The processing element 34 receives the PPG signals from the optical receivers 28. In some embodiments, the processing element 34 may sample the analog PPG signal from the optical receivers 28 to produce a digital form of the PPG signal. In other embodiments, the processing element 34 may receive the digital form of the PPG signal from the optical receivers 28.

In embodiments having the first optical receiver 28A and the second optical receiver 28B, the processing element 34 receives two PPG signals each time one of the transmitters 42 transmits an optical signal—one PPG signal is received from each optical receiver 28. The processing element 34 may perform a preliminary analysis that identifies or produces an output PPG signal based on the two received PPG signals. For instance, the processing element 34 may determine signal characteristics, such as an amplitude and a phase, of each PPG signal. In some embodiments, the processing element 34 may select one of the two PPG signals for subsequent use with determining a user's cardiac information, such as heart rate or pulse oximetry. For instance, the processor may discard one of the PPG signals having a lower signal quality (e.g., overall amplitude, excessive noise, etc.) than the other PPG signal by selecting the PPG signal having the higher amplitude and/or less noisy PPG signal as the output PPG signal. In other embodiments, the processing element 34 may combine the two PPG signals or generate a PPG signal based on the two PPG signals. For example, if the two PPG signals have sufficient amplitude and are not excessively noisy, then the processing element 34 may process or condition the two PPG signals such as by performing mathematical functions on them, like averaging, correlating, or so forth, to produce the output PPG signal. The mathematical functions may have the effect of enhancing or maximizing the cardiac component while reducing or minimizing the noise components. In embodiments, the processing element 34 may determine whether the cardiac component is strongly correlated between both PPG signals. In many cases, the noise components will be weakly correlated even if the cardiac component is strongly correlated. After this preliminary processing or analysis, the processing element 34 may utilize the resulting PPG signal to determine a heart rate of the user, which may be determined by calculating a frequency of the cardiac component or the number of PPG signal waveform peaks that occur within a minute.

In embodiments of the electronic fitness device 10 having optical transmitters 42 that transmit optical signals at different wavelengths, the processing element 34 may identify PPG signals having different wavelengths for use with determining a pulse oximetry. In embodiments having two optical receivers 28, the processing element 34 may identify two pairs of PPG signals for use with determining pulse oximetry. For example, a first pair of PPG signals may be output by the first and the second optical receivers 28A, 28B resulting from the third optical transmitter 42A3 transmitting an optical signal having a first wavelength—the Pulse Ox 1 wavelength. Similarly, a second pair of PPG signals may be output by the first and the second optical receivers 28A, 28B resulting from the fourth optical transmitter 42A4 transmitting an optical signal having a second wavelength—the Pulse Ox 2 wavelength. The processing element 34 may perform the above-described preliminary analysis on the first pair of PPG signals to produce a first wavelength PPG signal and the processing element 34 may perform the preliminary analysis on the second pair of PPG signals to produce a second wavelength PPG signal. The processing element 34 may then determine the AC and DC values of the cardiac components of the first wavelength PPG signal and the second wavelength PPG signal, respectively, which are utilized in EQ. 1 to determine the pulse oximetry indicator. The processing element may determine the user's pulse oximetry, or percentage of oxygen in the blood, based on the pulse oximetry indicator and a relationship stored in a memory element 32 that associates the pulse oximetry indicator and a value of the user's pulse oximetry. In embodiments, the relationship may be expressed as a lookup table stored in the memory element that includes a plurality of pulse oximetry indicators and their associated pulse oximetry values for one or more health and/or physiological characteristics. Health characteristics may include age, gender, weight, height and fitness class (i.e., overall physical fitness level). Physiological characteristics may include, but are not limited to, a heartbeat, heart rate, heart-rate variability, speed, distance traveled, calculating calories burned, body temperature, blood pressure, stress intensity level, body energy level, and the like. In embodiments, the processing element may identify a pulse oximetry value based on a determined pulse oximetry indicator (EQ. 1), one or more health characteristics (e.g., age, gender, and weight) and one or more physiological characteristics (e.g., heart rate and heart-rate variability).

Figure 8:
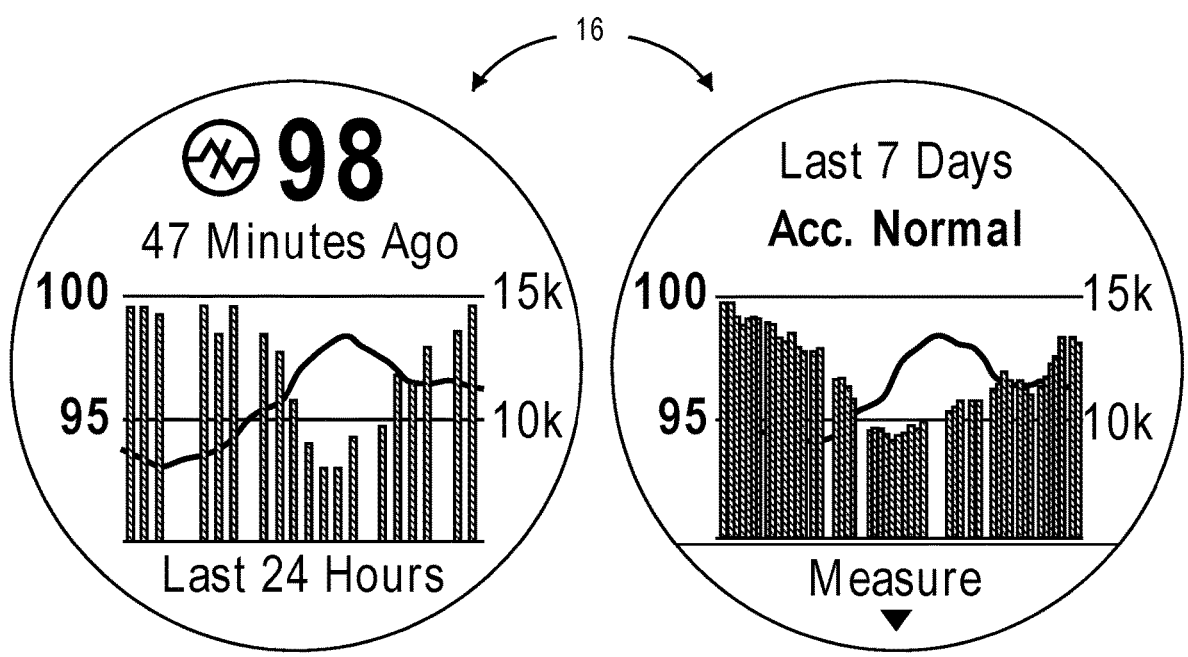
FIG. 8 is a plurality of screen captures of a display of the electronic fitness device displaying cardiac information of the user.
Figure 9:
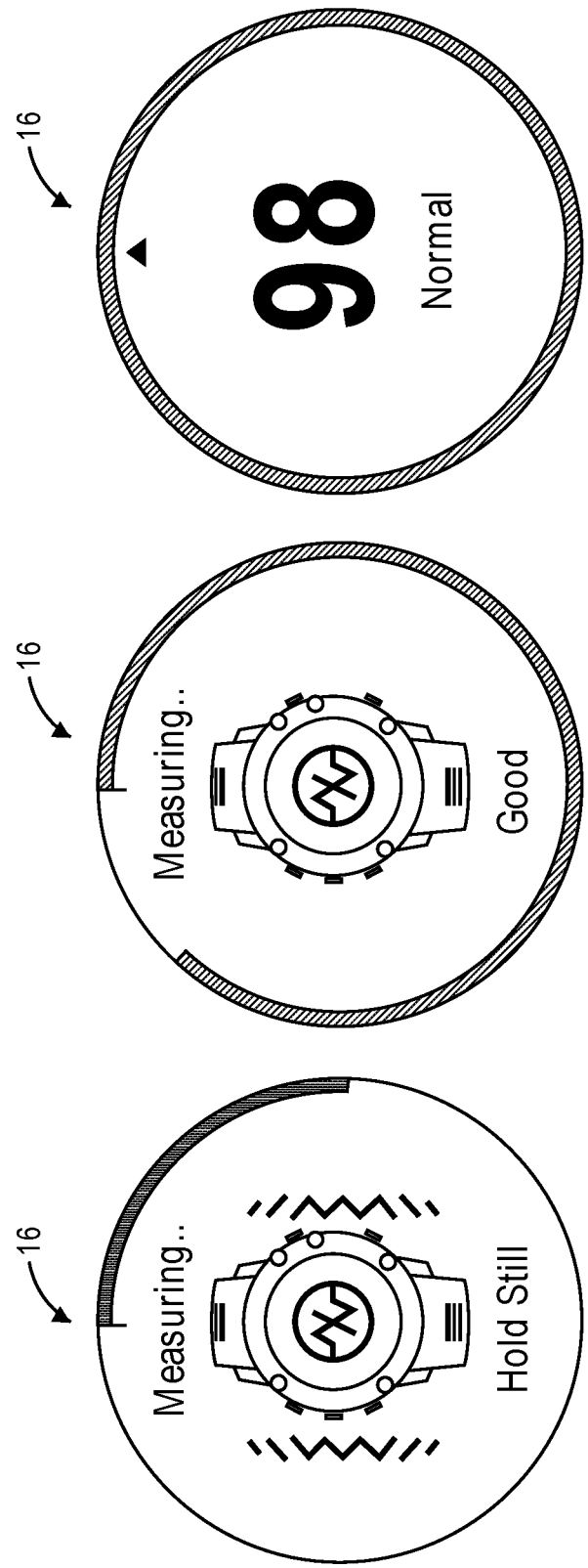
FIG. 9 is a plurality of screen captures of the display displaying a status of a measurement process for acquiring cardiac information.
Figure 10:
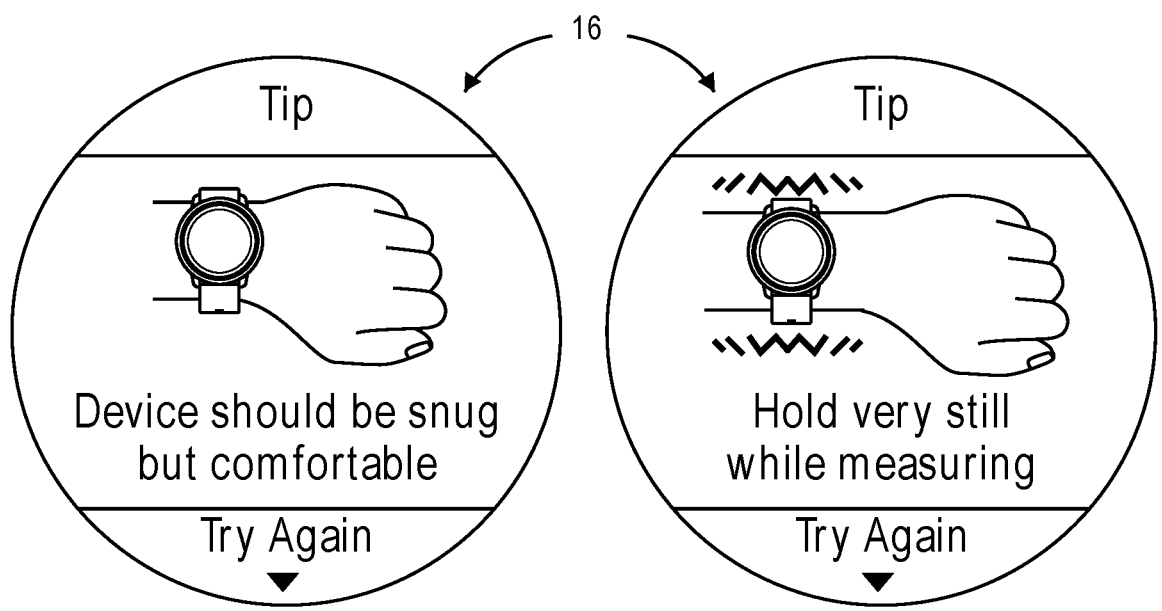
FIG. 10 is a plurality of screen captures of the display presenting tips for improving the performance of the measurement process for acquiring cardiac information.

The processing element 34 may also control the display 16 to present the determined cardiac information. Examples of screenshots of the display 16 displaying historically recorded pulse oximetrys for a given time period, such as a day or a week, are shown in FIG. 8. Examples of screenshots of the display 16 displaying a message to the user that a pulse oximetry measurement is in progress are shown in FIG. 9. Examples of screenshots of the display 16 presenting tips for improved measurement and performance provided to the user (a user of the electronic fitness device 10) are shown in FIG. 10.

The electronic fitness device 10 may operate as follows. The user may desire to determine his cardiac information, such as heart rate or pulse oximetry. He may utilize the user interface 18 to direct the processing element 34 to begin the process of determining the heart rate and/or the pulse oximetry. Alternatively, or additionally, the processing element 34 may have an operating mode in which it automatically initiates the process of determining the heart rate or pulse oximetry when a predetermined event occurs (e.g., heart-rate variability exceeding a predetermined threshold, body temperature exceeding a predetermined threshold, etc.) or on a periodic basis (e.g., every second, every minute, hourly, daily, etc.).

Figure 11:
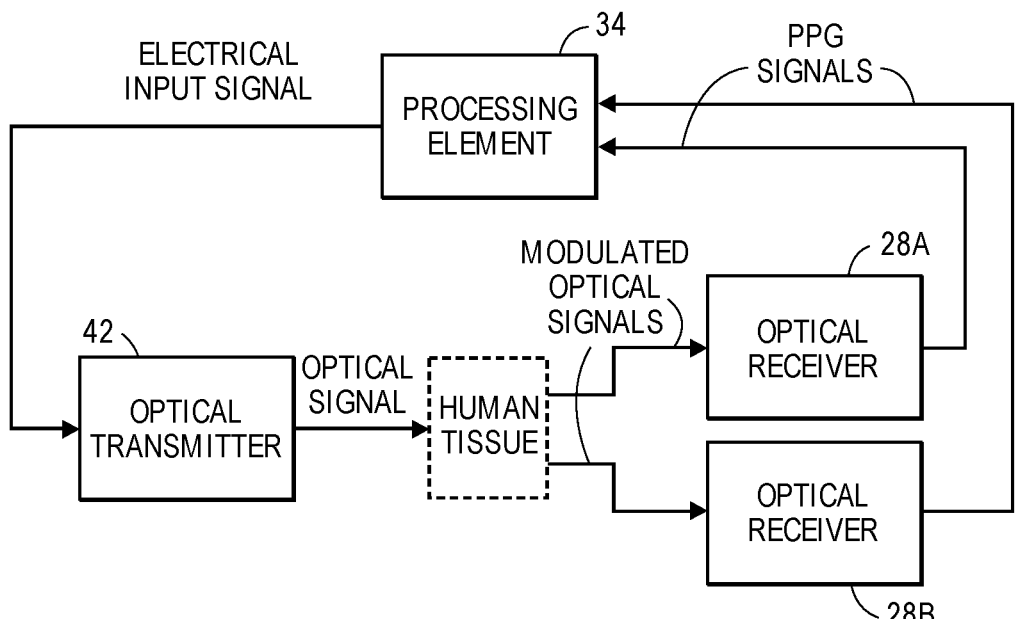
FIG. 11 is a block diagram illustrating the electronic components involved in emitting a plurality of optical signals, receiving reflections of the plurality of optical signals, and generating a PPG signal corresponding to each optical signal.

Referring to FIG. 11, the process of generating PPG signals is shown. The processing element 34 generates the electrical input signal or control signal and communicates it to the optical transmitter 42 during one time period. Depending on the type of cardiac information desired (heart rate or pulse oximetry), the processing element 34 may communicate the electrical input signal or control signal to a particular optical transmitter 42 or to multiple optical transmitters 42 (causing the optical transmitter(s) 42 to transmit the optical signal having a first wavelength). The optical transmitter 42 transmits the optical signal through a lens 30 into the user's skin (human tissue) for the first time period. Given that the electromagnetic radiation of the optical signal travels radially outward (in a 360-degree pattern) from the optical transmitter 42, reflections of the modulated optical signal are received by both optical receivers 28A, 28B through lens 30B and lens 30D. The reflections are received by the two optical receivers 28A, 28B whether the optical receivers 28 are both located in the same direction from (on the same side as) the optical transmitter 42 or opposing directions from (on opposite sides of) the optical transmitter 42. The optical receivers 28A, 28B each generate a PPG signal and communicate it to the processing element 34. The processing element 34 then performs the preliminary analysis on the two PPG signals described above in order to produce a single PPG signal for the first wavelength. A similar process occurs to produce a single PPG signal for a second wavelength. The processing element 34 may use the PPG signals corresponding to the first wavelength and the second wavelength, respectively, with determining a pulse oximetry indicator and a pulse oximetry for the user as detailed herein.

To determine the user's heart rate, in some embodiments, the processing element 34 generates the electrical input signal or control signal and communicates the signal to the first optical transmitter 42A1 of the first optical transmitter array 26A. The processing element 34 may generate and communicate the electrical input signal or control signal during a single time period, over multiple time periods, or continuously. The optical transmitter 42A1 transmits the optical signal, having a wavelength suitable for heart rate determination, through the lens 30A into the user's skin. Each optical receiver 28 receives reflections of the modulated optical signal and generates a corresponding PPG signal which is communicated to the processing element 34. The processing element 34 may then perform the preliminary analysis on the two PPG signals described above in order to produce a single heart rate PPG signal, which may be utilized to determine the user's heart rate by determining the frequency of the cardiac component or the number of PPG signal waveform peaks that occur within a minute.

In embodiments having a plurality of optical transmitter arrays 26A, 26B, the processing element 34 generates the electrical input signal or control signal and communicates the signal to the first optical transmitters 42A1, 42B1 of the first and second optical transmitter arrays 26A, 26B, respectively. The processing element 34 may generate and communicate the electrical input signal or the control signal to the optical transmitters 42A1, 42B1 simultaneously. Alternatively, the processing element 34 may communicate the electrical input signal or the control signal to the first optical transmitter 42A1 of the first optical transmitter array 26A during a first time period, and generate and communicate the electrical input signal to the first optical transmitter 42B1 of the second optical transmitter array 26B during a second time period. The first optical transmitter 42A1 transmits a first optical signal through the lens 30A and the first optical transmitter 42B1 transmits a second optical signal through the lens 30B into the user's skin—each optical signal having a wavelength suitable for heart rate determination. In embodiments where the first optical transmitter 42A1 transmits an optical signal during the first time period and the optical transmitter 42B1 transmits an optical signal during the second time period, four PPG signals are generated because each modulated optical signal is received through lens 30B and lens 30D by the first optical receiver 28A and the second optical receiver 28B, respectively. The processing element 34 may perform the preliminary analysis in stages, such as analyzing the two PPG signals resulting from the first optical signal transmitted by the first optical transmitter 42A1 followed by analyzing the two PPG signals resulting from the second optical signal transmitted by the first optical transmitter 42B1. Alternatively, the processing element 34 may analyze the four PPG signals simultaneously or nearly simultaneously in order to produce a single PPG signal. The processing element 34 then utilizes the PPG signal to determine the user's heart rate.

To determine the user's pulse oximetry, in some embodiments, the processing element 34 generates the electrical input signal or control signal and communicates it to the third optical transmitter 42A3 during a first time period and the fourth optical transmitter 42A4 during a second time period. The third optical transmitter 42A3 transmits the optical signal having a first wavelength (in the pulse ox 1 range) during the first time period, while the fourth optical transmitter 42A4 transmits the optical signal having a second wavelength (in the pulse ox 2 range) during the second time period. There are four PPG signals generated—two PPG signals resulting from the optical signal of the first wavelength transmitted by the third optical transmitter 42A3 and two resulting from the optical signal of the second wavelength transmitted by the fourth optical transmitter 42A4. The processing element 34 may perform the preliminary analysis in stages, such as analyzing the two PPG signals resulting from the optical signal of the first wavelength followed by analyzing the two PPG signals resulting from the optical signal of the second wavelength—which produces a first wavelength PPG signal and a second wavelength PPG signal. The processing element 34 determines the AC and DC values from the first and second wavelength PPG signals and utilizes them with the equation EQ. 1 to calculate the pulse oximetry indicator. The processing element 34 may then determine the user's pulse oximetry based on the pulse oximetry indicator and a relationship stored in the memory element 32 that associates the pulse oximetry indicator and a value of the user's pulse oximetry.

In some cases, the motion component of the PPG signals for determining heart rate or pulse oximetry is sufficiently large to prevent the processing element 34 from making an accurate determination of the user's heart rate or pulse oximetry. In such cases, the optical transmitters 42 that transmit optical signals having a wavelength in the motion range are utilized to reduce the motion component of other PPG signals generated over a different or a corresponding period of time. The processing element 34 may generate and communicate an electrical input signal or a control signal to the second optical transmitter 42A2 of the first optical transmitter array 26A and the second optical transmitter 42B2 of the second optical transmitter array 26B. The processing element 34 may cause transmission of optical signals for use with motion filter during or after the time periods for generating and communicating the electrical input signal or control signals to transmit optical signals for use with determining the user's heart rate or pulse oximetry. The optical transmitters 42A2, 42B2 each transmit the optical signal having a wavelength in the motion range. The reflections of modulated optical signals from the user's skin are received by the optical receivers 28A, 28B, and PPG signals are generated by the optical receivers 28A, 28B. Two PPG signals are generated by the optical receivers 28A, 28B if the optical transmitters 42A2, 42B2 transmit the optical signal simultaneously. Four PPG signals are generated by the optical receivers 28A, 28B if the optical transmitters 42A2, 42B2 transmit the optical signal sequentially (at different time periods). The processing element 34 performs preliminary analysis on the PPG signals generated by the optical receivers 28A, 28B either in stages or simultaneously to produce a motion PPG signal.

In embodiments, the processing element 34 may produce a motion-compensated PPG signal by reducing a motion component of the PPG signal based on another PPG signal. For example, the processing element 34 may identify a pair of PPG signals with similar optical paths, but different wavelengths, and use one of the two PPG signals to reduce motion components of the other PPG signal. In an embodiment, a first PPG signal may be generated using optical transmitter 42A1 having a wavelength in the heart rate range and a second PPG signal may be generated using optical transmitter 42A2 having a wavelength in the motion range. A motion-compensated first PPG signal may be generated by using the second PPG signal to reduce the motion component of the first PPG signal. In embodiments having two pairs of PPG signals, where each pair has a similar optical path, the processing element 34 may produce a first motion-compensated PPG signal by reducing a motion component of a first PPG signal based on a second PPG signal (a first pair), produce a second motion-compensated PPG signal by reducing a motion component of a third PPG signal based on a fourth PPG signal (a second pair), and produce a first wavelength PPG signal based on the first and the second motion-compensated first PPG signals.

In embodiments where the processing element 34 is determining the user's heart rate, the processing element 34 may perform mathematical signal processing or conditioning operations, such as correlation, averaging, or the like, on the heart rate PPG signal and the motion PPG signal, wherein the motion PPG signal may be used to reduce the motion component of the heart rate PPG signal. The operations may produce a filtered heart rate PPG signal, which is then utilized to determine the user's heart rate in a manner discussed above.

In embodiments where the processing element 34 is determining the user's pulse oximetry, the processing element 34 may perform mathematical signal processing or conditioning operations, such as correlation, averaging, or the like, on the first wavelength PPG signal and the motion PPG signal in a first operation and on the second wavelength PPG signal and the motion PPG signal in a second operation wherein the motion PPG signal may be used to reduce the motion component of the first wavelength PPG signal and the second wavelength PPG signal. The operations may produce a filtered first wavelength PPG signal and a filtered second wavelength PPG signal, which are then utilized to determine the user's pulse oximetry in a manner discussed above.

The electronic fitness device 10 may achieve PPG signal differentiation in a number of ways. The spatial configuration and control of the optical transmitter arrays 26 and the optical receivers 28 provide different lengths/distances and different directions for each optical signal to travel from each optical transmitter 42 to an optical receiver 28, resulting in PPG signal differentiation. For example, the optical signal transmitted by any of the four optical transmitters 42 of the first optical transmitter array 26 travels a first path length to the first optical receiver 28A and a second (different) path length to the second optical receiver 28B. The optical signal transmitted by any of the two optical transmitters 42B1, 42B2 of the second optical transmitter array 26B travels in a first direction to the first optical receiver 28A and a second, opposing direction to the second optical receiver 28B.

PPG signals may also be differentiated in the way that the PPG digital data is formed. For example, a first analog PPG signal may be sampled at a first sampling rate, such as one sample per every 10 ms to produce a first PPG signal that is ready for the preliminary analysis. A second analog PPG signal may be sampled at the same first sampling rate, but which is offset, shifted, or delayed in time, such as one sample per every 10 ms plus 5 ms to produce a second PPG signal that is ready for the preliminary analysis.

Figure 12:
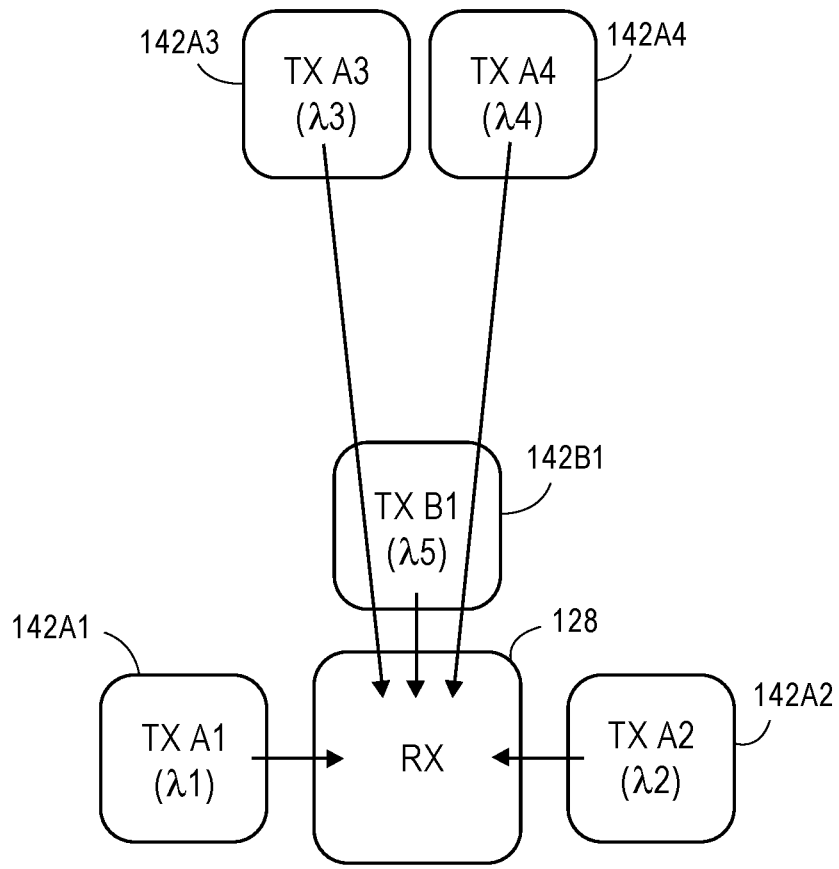
FIG. 12 is a schematic view of an embodiment of a plurality of optical transmitters and an optical receiver illustrating pathways of a plurality of optical signals transmitted by each of the optical transmitters and received by an optical receiver.
Figure 13:
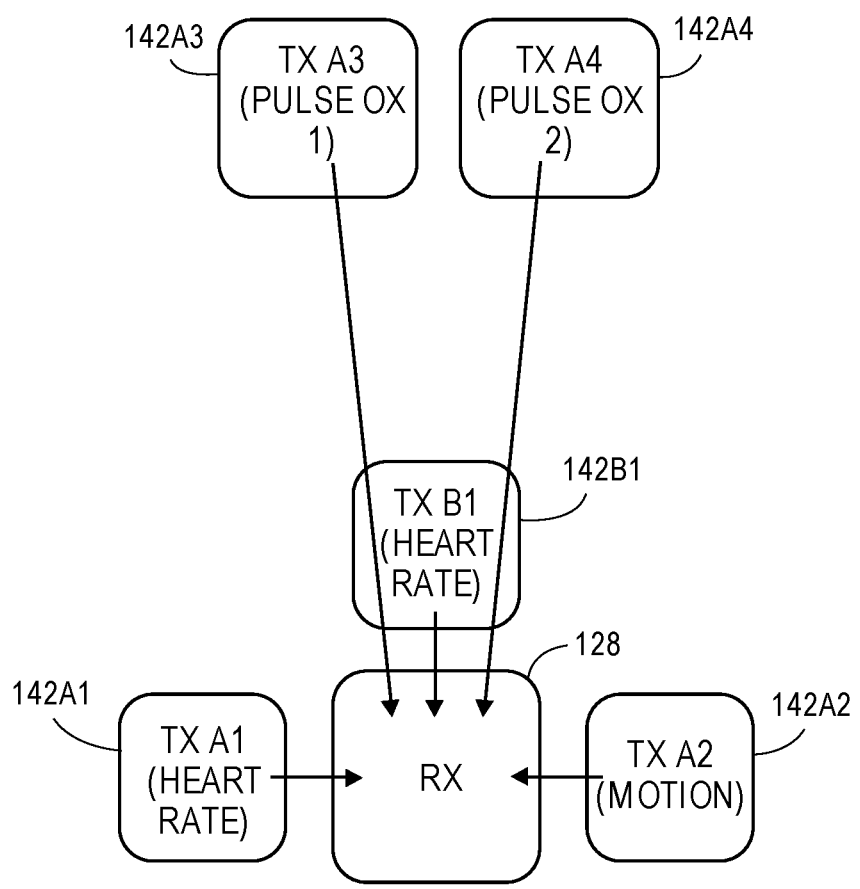
FIG. 13 is another schematic view of the optical transmitters and optical receiver of FIG. 12, the optical transmitters configured to output optical signals utilized to implement the indicated functions based on the optical signals received by the optical receiver.

In other embodiments, as shown in FIGS. 12 and 13, the electronic fitness device 10 may include a configuration of optical transmitters 142 and an optical receiver 128. The optical transmitters 142 are substantially the same in structure and operation as the optical transmitters 42 discussed above and include a first optical transmitter 142A1 transmitting the optical signal having a first wavelength ($\lambda 1$), a second optical transmitter 142A2 transmitting the optical signal having a second wavelength ($\lambda 2$), a third optical transmitter 142A3 transmitting the optical signal having a third wavelength ($\lambda 3$), a fourth optical transmitter 142A4 transmitting the optical signal having a fourth wavelength ($\lambda 4$), and a fifth optical transmitter 142B1 transmitting the optical signal having a fifth wavelength ($\lambda 5$). The optical receiver 128 is substantially the same in structure and operation as either of the optical receivers 28A, 28B.

FIG. 13 depicts exemplary functions processing element 34 utilizes each optical transmitter 142 based on the wavelength of the optical signal transmitted. For example, processing element 34 may control the first optical transmitter 142A1 and the fifth optical transmitter 142B1 to transmit an optical signal suitable for the processing element 34 to determine a user's heart rate. Similarly, the processing element 34 may control the second optical transmitter 142A2 to transmit an optical signal used to eliminate or reduce (filter) the motion component of the PPG signal. The processing element 34 may control the third optical transmitter 142A3 and the fourth optical transmitter 142A4 to transmit a first and a second optical signal, respectively, for determining pulse oximetry. The range of wavelengths associated with each subsequent use or function of the PPG signal resulting from the optical signals by the processing element 34 is shown in FIG. 4.

Similar to optical transmitters 42 and optical receivers 28, the optical transmitters 142 and the optical receiver 128 are positioned in openings on the bottom wall 36 of the housing 12. The optical transmitters 142 are generally positioned relative to the optical receiver 128, with the first optical transmitter 142A1, the second optical transmitter 142A2, and the fifth optical transmitter 142B1 each positioned adjacent to one side of the optical receiver 128, such that the optical receiver 128 has a different one of the optical transmitters 142 adjacent to three of its four sides. The relative positions of the optical transmitters 142 adjacent to the optical receiver 128 may be changed and still fall within the scope of the present technology. For example, the relative positions of the second optical transmitter 142A2 and the fifth optical transmitter 142B1 may be swapped and still be within the scope of the present technology.

The third optical transmitter 142A3 and the fourth optical transmitter 142A4 are positioned adjacent one another and at a substantially equal distance from the optical receiver 128, the distance being greater than a distance between the optical receiver and any of the first, second, or fifth optical transmitters 142. In various embodiments, the optical receiver 128 may be positioned at one edge of the bottom wall 36 while the third optical transmitter 142A3 and the fourth optical transmitter 142A4 are positioned at the opposing edge of the bottom wall, so as to maximize the distance that the optical signals transmitted by the third optical transmitter 142A3 and the fourth optical transmitter 142A4 travel to the optical receiver 128. Increasing the distance or path length that the optical signals of the red wavelength and the infrared wavelength for determining pulse oximetry may result in a greater SNR and/or SMNR of the cardiac component of the resulting PPG signal.

The processing element 34 communicates with the optical transmitters 142 and the optical receiver 128 in substantially the same fashion as described above with optical transmitters 42 and the optical receivers 28. And the electronic fitness device 10 functions similarly as discussed above, but with the following exceptions related to the optical transmitters 142 and the optical receiver 128.

To determine the user's heart rate, in embodiments, the processing element 34 may generate and communicate an electrical input signal or a control signal to the first optical transmitter 142A1 and the fifth optical transmitter 142B1 during a first time period and a second time period, respectively. The processing element 34 may generate and communicate the electrical input signal or the control signal to the second optical transmitter 142A2 during the first time period, the second time period, and/or a third time period. The first optical transmitter 142A1 and fifth optical transmitter 142B1 transmit a first and a second optical signal having a wavelength in the heart rate range during the first and the second time periods, respectively. The second optical transmitter 142A2 transmits a third optical signal having a wavelength in the motion range for use by the processing element 34 with eliminating or reducing (filtering) the motion component of the PPG signal. Reflections of the modulated optical signals are received by the optical receiver 128, which generates two PPG signals, one for each modulated optical signal associated with the heart rate range, and a PPG signal associated with the motion range. The processing element 34 performs the preliminary analysis on the two PPG signals and produces one heart rate PPG signal, which may have a motion component removed based on the PPG signal associated with motion, from which the user's heart rate is determined.

Alternatively, the processing element 34 may generate and communicate an electrical input signal or a control signal to just the first optical transmitter 142A1 which transmits an optical signal having a wavelength in the heart rate range. The optical receiver 128 receives the modulated optical signal and generates a PPG signal which is utilized to determine the user's heart rate.

To determine the user's pulse oximetry, the processing element 34 may generate an electrical input signal or a control signal and communicate the signal to the third optical transmitter 42A3 and the fourth optical transmitter 42A4. The third optical transmitter 42A3 may transmit the optical signal having a first wavelength, while the fourth optical transmitter 42A4 may transmit the optical signal having a second wavelength. The processing element 34 utilizes the two PPG signals to determine the AC and DC values of the first and second wavelength signals and uses the determined AC and DC values with the equation EQ. 1 to calculate a pulse oximetry indicator. The processing element 34 may determine the user's pulse oximetry based on the pulse oximetry indicator and a relationship stored in the memory element 32 that associates the pulse oximetry indicator and a value of the user's pulse oximetry.

When the motion component of the PPG signals for determining heart rate or pulse oximetry is sufficiently large, processing element 34 may utilize the optical transmitter 142A2 to transmit an optical signal, the reflection of which will be used by the optical receiver 128 to create a motion PPG signal, that can be utilized to reduce the motion component of other PPG signals generated over a different or a corresponding period of time. Alternatively, the optical transmitter 142A2 may be utilized automatically for every determination of heart rate or pulse oximetry. In either case, the processing element 34 may generate and communicate the electrical input signal or the control signal to the second optical transmitter 142A2 during a time period after the time periods for generating and communicating the electrical input signal for heart or pulse oximetry determination. The optical transmitter 142A2 transmits the optical signal having a wavelength in the motion range. The modulated optical signal is received by the optical receiver 128 and a motion PPG signal is generated.

In embodiments where the processing element 34 is determining the user's heart rate, the processing element 34 may perform mathematical signal processing or conditioning operations, such as correlation, averaging, or the like, on the heart rate PPG signal and the motion PPG signal, wherein the motion PPG signal may be used to reduce the motion component of the heart rate PPG signal. The operations may produce a filtered heart rate PPG signal, which is then utilized to determine the user's heart rate in a manner discussed above. In embodiments, the processing element 34 may produce a motion-compensated PPG signal by reducing a motion component of the PPG signal based on another PPG signal.

In embodiments where the processing element 34 is determining the user's pulse oximetry, the processing element 34 may perform mathematical signal processing or conditioning operations, such as correlation, averaging, or the like, on the first wavelength PPG signal and the motion PPG signal in a first operation and on the second wavelength PPG signal and the motion PPG signal in a second operation wherein the motion PPG signal may be used to reduce the motion component of the first wavelength PPG signal and the second wavelength PPG signal. The operations may produce a filtered first wavelength PPG signal and a filtered second wavelength PPG signal, which are then utilized to determine the user's pulse oximetry in a manner discussed above.

After the cardiac information has been determined, the processing element 34 may then control the display 16 to display the heart rate or pulse oximetry.

The following paragraphs describe additional and/or alternative embodiments. For PPG sensors (e.g., optical cardiac monitor, pulse-oximetry monitor, etc.), motion artifacts within in a PPG signal may be influenced by an effective path taken by the optical signal after it was output by an optical transmitter TX (e.g., LED), passed through the tissue, and is reflected to an optical receiver RX (e.g., photodiode) and used to generate the PPG signal. When the optical signal passes through different paths through the user's skin (from a plurality of optical transmitters TX to one or more optical receivers RX), the processing element 34 may utilize the generated individual PPG signals to generate a resultant PPG signal with a cardiac component to motion noise (artifact) ratio (SMNR) which is better than the SMNR of the individual components. For example, the processing element 34 may utilize a plurality of PPG signals generated substantially simultaneously to generate an average resultant PPG signal.

In some embodiments, more than one motion reference signal is generated with the optical signal that passes through different paths through the user's skin. In some embodiments, a motion reference signal is generated for every path used for determination of heart rate. When the optical signal passes through different paths through the user's skin (from a plurality of optical transmitters 42 to one or more optical receivers 28), the processing element 34 may utilize the generated signals to identify different motion artifacts resulting from one motion, such as the user raising his arm. For example, the processing element 34 may utilize a plurality of motion reference signals generated substantially simultaneously to identify different motion artifacts resulting from one motion. In other implementations, the processing element 34 may utilize a plurality of motion reference signals generated substantially simultaneously to identify paths with high motion artifact modulation.

Figure 14A:
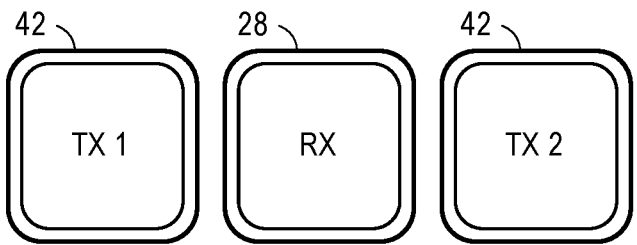
FIG. 14A is another schematic view of an additional embodiment of various configurations of optical transmitters and optical receivers.

In some embodiments, the electronic fitness device 10 may include two or more optical transmitters 42 that are used concurrently or independently to generate a PPG signal having a cardiac component. The two or more optical transmitters 42 may have different spectral properties. An example of an electronic fitness device 10 including two optical transmitters 42 and an optical receiver 28 is shown FIG. 14A.

Figure 14B:
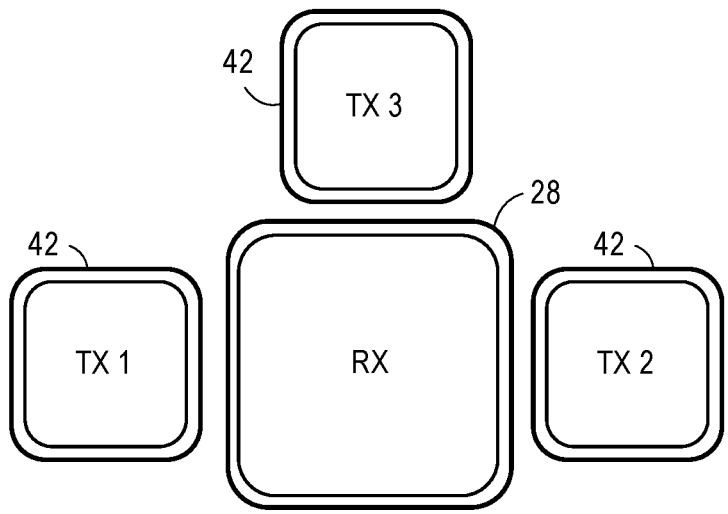
FIG. 14B is another schematic view of an additional embodiment of various configurations of optical transmitters and optical receivers.

In embodiments, the electronic fitness device 10 may have a housing 12 utilizing a larger lens 30 over the optical receiver 28 than a lens 30 placed over the optical transmitters 42. As shown FIG. 14B, each optical transmitter 42 may be positioned adjacent to a side of the lens 30 associated with an optical receiver 28.

Figure 14C:
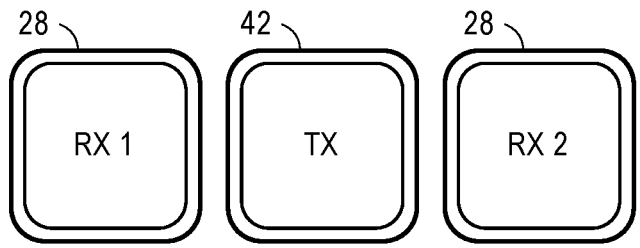
FIG. 14C is another schematic view of an additional embodiment of various configurations of optical transmitters and optical receivers.

In some embodiments, the electronic fitness device 10 may include two or more optical receivers 28 that are used concurrently or independently to generate a PPG signal having the cardiac component. The two or more optical receivers 28 may have different spectral properties. Examples of such an electronic fitness device 10 having one or more optical transmitters 42 and a plurality of optical receivers 28 are shown FIG. 14C.

Figure 14D:
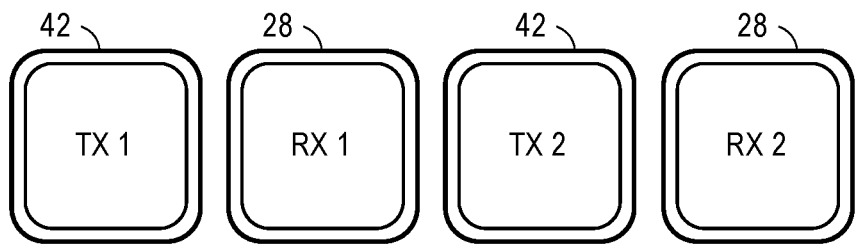
FIG. 14D is another schematic view of an additional embodiment of various configurations of optical transmitters and optical receivers.
Figure 14E:
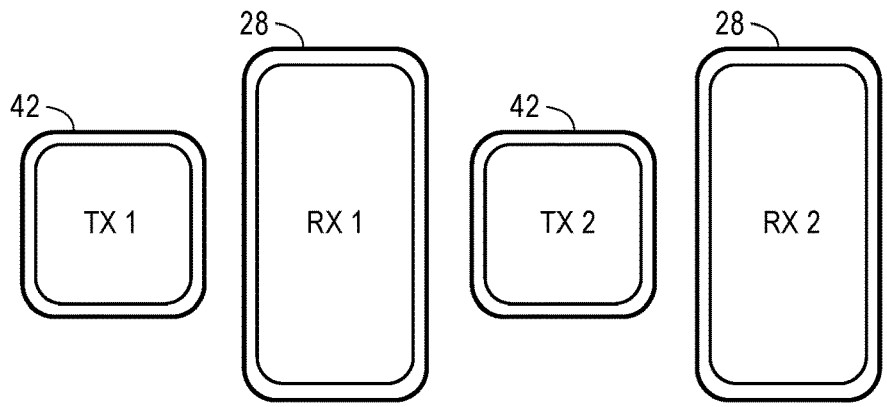
FIG. 14E is another schematic view of an additional embodiment of various configurations of optical transmitters and optical receivers.

In embodiments as shown in FIG. 14D, the electronic fitness device 10 may include a plurality of optical transmitters 42 and a plurality of optical receivers 28. In embodiments as shown in FIG. 14E, the electronic fitness device 10 may have a housing 12 utilizing a larger lens 30 over the optical receivers 28 than a lens 30 placed over the optical transmitters 42.

The use of two or more optical transmitters 42 and/or two or more optical receivers 28 with different spectral properties enables the processing element 34 to take advantage of complex spectral properties of the optical signal used to generate one or more of the PPG signal and the reference signal. For example, an optical transmitter 42 with center wavelength of 542 nm may be used together with an optical transmitter 42 with a center wavelength of 577 nm to generate a combined optical transmitter 42 with two spectral peaks—one at a wavelength of 542 nm and another at 577 nm. The use of two or more optical transmitters 42 and/or optical receivers 28 with different spectral properties also enables the processing element 34 to implement time-varying techniques based on the spectral properties of the optical signal used to generate one or more of the PPG signal and the reference signal. For example, the processor element 34 may control an optical transmitter 42 with center wavelength of 542 nm for use with for some users or during some activities, and then, at another time, the processing element 34 may control an optical transmitter 42 with center wavelength of 577 nm for use with another user or during other activities.

In embodiments of electronic fitness device 10 having a plurality of optical receivers 28, multiple PPG signals and/or motion reference signals may be generated simultaneously or substantially simultaneously by the electronic fitness device 10 because the processing element 34 may control each receiver 28 to generate one or more of the PPG signal and the reference signal. For example, the processing element 34 may control two or more optical transmitters 42 to output the optical signal at the same time (simultaneously) and control at least two receivers 28 to generate a plurality of PPG signals based on reflections of the optical signal. In other implementations, the processing element 34 may control two or more optical transmitters 42 to cyclically and sequentially turn on (enable the optical signal output) and turn off (disable the optical signal output) for short time periods, and the processing element 34 may control one or more optical receivers 28 to generate a plurality of PPG signals. For example, the processing element 34 may control the one or more optical receivers 28 to generate a PPG signal during time periods corresponding to the output of the optical signal. A first PPG signal may be captured by an optical receiver 28 during a first short time period corresponding to a first time period of the optical signal output by a first optical transmitter 42, followed by a second PPG signal being captured by the same or different optical receiver 28 during a second short time period corresponding to a second time period of the optical signal output by a second optical transmitter 42. In other embodiments, the processing element 34 may control one optical transmitter 42 to output the optical signal and two or more optical receivers 28 to generate multiple PPG signals substantially simultaneously.

Various combinations of the above techniques, and other known techniques may be used to generate a plurality of PPG signals substantially simultaneously. The plurality of PPG signals may be generated based on a plurality of reflections of the optical signal from the tissue of the user's skin, each reflection following a substantially different effective path than other reflections. The substantially different effective paths may be accomplished by implementing different spacing between an optical transmitter 42 and an optical receiver 28, different positioning of an optical transmitter 42 and/or an optical receiver 28, using optical transmitters 42 having different optical signal wavelengths, using wavelength-discriminating optical receivers 28 with a multiwavelength source, or any combination thereof.

As shown in FIG. 15, effective path differentiation for the multiple PPG signals may be accomplished by having multiple optical receivers 28 positioned on the tissue at different distances from an optical transmitter TX such that the optical signal received by each optical receiver 28 through a different effective path from the optical transmitter 42.

As shown in FIG. 16, effective path differentiation for the multiple PPG signals may be accomplished by having multiple optical transmitters 42 positioned on the tissue at different distances from an optical receiver 28 such that the optical signal from each optical transmitter 42 passes through a different effective path to the optical receiver 28. The multiple optical transmitters 42 may output the optical signal simultaneously or sequentially.

As shown in FIG. 17, effective path differentiation for the multiple PPG signals may be accomplished by having multiple optical receivers 28 positioned in different directions from an optical transmitter 42 such that the optical signal from each optical transmitter 42 passes through a different effective path to the optical receivers 28.

As shown in FIG. 18, effective path differentiation for the multiple PPG signals may be accomplished by having multiple optical transmitters 42 positioned such that the optical signal output by the optical transmitter 42 is received from different directions by the optical receiver 28, where the optical signal from each optical transmitter 42 passes through a different effective path to the optical receiver 28.

In some embodiments, the electronic fitness device 10 may output the optical signal having different wavelengths, as shown in FIGS. 19 and 20. Due to tissue spectral absorption properties, the optical signal having different wavelengths is capable of penetrating or reaching different regions of the user's skin and tissue. As detailed above, processing element 34 may control optical transmitter 42 (TX1) to output the optical signal having a first wavelength and the optical receiver 28 utilizes a reflection of the optical signal to generate a PPG signal having a cardiac component and the processing element 34 may control optical transmitter 42 (TX2) to output the optical signal that is received by the optical receiver 28 to generate a reference signal in a manner to be responsive to the motion artifact component of the PPG signal.

The electronic fitness device 10 may accomplish effective path differentiation for the multiple PPG signals by utilizing multiple optical transmitters 42 that emit the optical signal at different wavelengths to an optical receiver 28. As shown in FIG. 19, the processing element 34 of the electronic fitness device 10 may control optical transmitter 42 (TX1) to output the optical signal at a first wavelength and optical transmitter 42 (TX2) to output the optical signal at a second wavelength. An optical receiver 28 may receive reflections of the optical signal output by both optical transmitters 42 to generate two PPG signals. In embodiments, a first optical transmitter 42 (TX1) and a second optical transmitter (TX2) may be located in a common place in a housing 12 of the electronic fitness device 10 (under one lens 30). Alternatively, the first optical transmitter (TX1) and the second optical transmitter (TX2) may be located in different location in the housing 12 of the electronic fitness device 10 (under separate lenses 30).

The electronic fitness device 10 may accomplish effective path differentiation for the multiple PPG signals by utilizing multiple optical transmitters 42 that emit the optical signal at different wavelengths or a single optical transmitter 42 that emits the optical signal at multiple wavelengths to more than one optical receiver 28 configured to receive substantially different range of wavelengths. As shown in FIG. 20, the electronic fitness device 10 may accomplish effective path differentiation for the multiple PPG signals by utilizing multiple optical transmitters 42 that emit the optical signal at different wavelengths to multiple optical receivers 28 that generate each PPG signal, where each optical receiver 28 is configured to substantially receive different range of wavelengths than the other optical receivers 28. The processing element 34 of the electronic fitness device 10 may control a first optical transmitter 42 (TX1) to output the optical signal at a first wavelength and a second optical transmitter 42 (TX2) to output the optical signal at a second wavelength, sequentially or simultaneously. In some implementations, the two optical transmitters 42 include a first optical transmitter 42 that produces the optical signal with multiple optical signal wavelengths (e.g. broadband optical transmitter). Two optical receivers 28 may receive reflections of the optical signal at different wavelengths output by one or more optical transmitters 42 to generate two PPG signals.

In embodiments, each optical receiver 28 may include a filter or a lens 30 including a filter configured to substantially accept optical signal(s) with desired wavelengths and substantially reject other optical signals (wavelengths). A first optical receiver 28 (RX1) may receive reflections of the optical signal output by a first optical transmitter 42 (TX1) and a second optical receiver 28 (RX2) may receive reflections of the optical signal output by a second optical transmitter 42 (TX2). In embodiments, a first optical transmitter 42 (TX1) and a second optical transmitter 42 (TX2) are one source which transmits the optical signal at multiple wavelengths (e.g. broadband optical transmitter, white light, etc.). In embodiments, a first optical receiver 28 (RX1) and a second optical receiver (RX2) are an array of photoelectric devices, with at least some of the photoelectric devices configured to preferentially accept optical signals with wavelengths which are different from optical signal wavelengths preferentially accepted by other devices in the array. In some implementations, the array is an array of optical receivers 28 with different optical filters for at least some of the array elements.

In some embodiments, the electronic device 10 may utilize optical signal guides (e.g. optical fibers) to implement path diversity. For example, optical signal guides may be used to spatially distribute the optical signal generated by an optical transmitter 42 to multiple locations on the skin by dividing the generated optical signal into portions each of which is guided to and transmitted into the skin at different locations on the skin. Similarly, the optical signal may be optically collected at multiple locations on the skin and channeled to one or more optical receivers 28, where the one or more optical receivers 28 may capture the optical signal concurrently or sequentially.

These configurations and techniques, or combinations thereof, may be utilized to implement path diversity amongst a plurality of PPG signals that are analyzed by a processing element 34 to determine physiological characteristics, such as heart rate, heart rate variability, blood pressure, stress intensity level, and body energy level. For example, spacing between an optical transmitter 42 and an optical receiver 28 and the relative positioning or different wavelengths may be used simultaneously or in any combination to achieve path diversity. The electronic fitness device 10 generates multiple PPG signals substantially simultaneously using reflections of the optical signal that penetrates tissue proximate to the housing 12 with substantially different effective paths. The processing element 34 may combine two or more of the PPG signals to improve the signal to motion-noise ratio (SMNR) of the resulting PPG signal relative to SMNR of the separate PPG signals.

In some embodiments, the processing element 34 may combine multiple PPG signals by adding the PPG signals together. The processing element 34 may add the PPG signals by implementing analog summation. For example, when optical signals from multiple optical transmitters 42 are received by the one optical receiver, as shown in FIG. 18, the optical transmitters 42 may emit the optical signal substantially simultaneously. The optical signal may combine in tissue after it is emitted and the optical receiver 28 may receive the sum of the combined optical signal and convert the received optical signal into a PPG signal. Alternatively, when optical signals from multiple optical transmitters 42 are received by the one optical receiver, as shown in FIG. 18, the optical transmitters 42 may emit the optical signal sequentially such that only one optical transmitter 42 emits the optical signal at a time. The optical receiver 28 may receive the optical signal from each optical transmitter 42 separately and convert the more than one received optical signal into more than one PPG signals. The processing element 34 may add the more than one PPG signals using digital summation to generate a resultant PPG signal. Alternatively, when optical signals from multiple optical transmitters 42 are received by the multiple optical receivers 28, as shown in FIG. 20, the processing element 34 may add the PPG signals using digital summation to generate a resultant PPG signal (after each optical receiver 28 generates a PPG signal based on the intensity of the optical signal received by the optical receiver 28).

In some embodiments, the processing element 34 combines multiple PPG signals by individually weighting each PPG signal by a signal quality metric determined by the processing element 34 for the PPG signal and then summing the weighted PPG signals. The processing element 34 may select any signal quality metric for each of the multiple PPG signals that at least partially quantifies signal to noise ratio (SNR) of the PPG signal, or expectation of the signal to noise ratio of the PPG signal. For example, in implementations, the signal quality metric for the PPG signal may be the ratio of the power of cardiac signal component of the PPG signal to the power of the remaining signal components in the PPG signal. In one implementation, the cardiac component of the PPG signal is the signal represented by the strongest spectral peak in the spectral representation of the PPG signal after identification and rejection of known interference components such as the motion cadence component. This metric partially quantifies the SNR of the PPG signal.

In embodiments, the electronic fitness device 10 generates a motion reference signal corresponding to one or more of the multiple PPG signals, each of which is generated using the optical signal that traveled along different effective paths through the tissue. For example, the electronic fitness device 10 may include a plurality of pairs of optical transmitters 42, where each pair includes one optical transmitter 42 outputting the optical signal used to generate a motion reference signal and another optical transmitter 42 outputting the optical signal used to generate a PPG signal. The processing element 34 may use the amplitude or other characteristics of the motion reference signal to quantify an expectation of SNR of a corresponding PPG signal. In one embodiment, the electronic fitness device 10 includes an optical transmitter 42 having a wavelength that maximizes motion-signal modulation relative to cardiac signal modulation, as described above.

In embodiments, one or more motion-wavelength reference signals may be generated to correspond to at least two PPG signals. Alternatively, one motion-wavelength reference signal may be generated for each of a plurality of corresponding PPG signals. The processing element 34 may use one or more characteristics of the motion reference signal as a signal quality metric for a corresponding PPG signal. In embodiments, the processing element 34 may combine the multiple PPG signals into a resultant PPG signal using a function of the multiple signal quality metrics.

In an embodiment, the processing element 34 may determine the power of the motion reference signal divided by the sum of the powers of all of the motion reference signals as a characteristic of the motion reference signal used as the signal quality metric. In another embodiment, the processing element 34 may determine the power of AC component of the motion reference signal divided by the sum of the AC powers of all of the motion reference signals as a characteristic of the motion reference signal used as the signal quality metric. In an implementation, the function of the multiple signal quality metrics is a weighted sum of the multiple PPG signals, where the weights are the signal quality metrics corresponding to the each of the multiple PPG signals. In other words, a first signal quality metric corresponding to a first PPG signal (of the multiple PPG signals) is the weight for the first PPG signal in the weighted sum of the multiple PPG signals. Similarly, a second signal quality metric corresponding to a second PPG signal is the weight for the second PPG signal in the weighted sum of the multiple PPG signals. The processing element 34 may similar weight other PPG signals of the multiple PPG signals to obtain the resultant PPG signal. In an implementation, each of the multiple PPG signals is divided by a signal representing substantially the DC component of the signal to obtain the corresponding DC-normalized PPG signal. The resultant PPG signal is then obtained by combining resulting multiple DC-normalized PPG signals using a function of the multiple signal quality metrics.

Although the technology has been described with reference to the embodiments illustrated in the attached drawing figures, it is noted that equivalents may be employed and substitutions made herein without departing from the scope of the technology as recited in the claims.

Having thus described various embodiments of the technology, what is claimed as new and desired to be protected by Letters Patent includes the following:

1. An electronic fitness device comprising:
   a housing including a bottom wall and one or more side walls;
   a first optical transmitter array positioned in a first opening on the bottom wall and including a first optical transmitter configured to transmit a first optical signal having a first wavelength and a second optical transmitter configured to transmit a second optical signal having a second wavelength;
   a first lens covering the first optical transmitter array and configured to direct the first and second optical signals into the skin of a user;
   a first optical receiver positioned in a second opening on the bottom wall at a first distance from the first optical transmitter array, the first optical receiver configured to receive optical signals modulated by the skin of the user and generate a first photoplethysmogram (PPG) signal resulting from the first optical signal and a second PPG signal resulting from the second optical signal;
   a second lens covering the first optical receiver and configured to direct optical signals from the skin to the first optical receiver;
   a second optical receiver positioned in a third opening on the bottom wall at a second distance from the first optical transmitter array, the second optical receiver configured to receive optical signals modulated by the skin of the user and generate a third PPG signal resulting from the first optical signal and a fourth PPG signal resulting from the second optical signal;
   a third lens covering the second optical receiver and configured to direct optical signals reflected from the skin to the second optical receiver; and
   a processing element in electronic communication with the first optical transmitter array and the first and second optical receivers, the processing element configured to:
     control the first optical transmitter to transmit the first optical signal during a first period of time,
     control the second optical transmitter to transmit the second optical signal during a second period of time,
     receive the PPG signals from the first optical receiver and the second optical receiver,
     identify a component of the first PPG signal that is substantially correlated with one or more components of the third PPG signal,
     produce a first wavelength PPG signal based on the correlation of the first PPG signal and the third PPG signal,
     produce a second wavelength PPG signal related to the second wavelength and based on the second PPG signal and the fourth PPG signal, and
     determine cardiac information of the user based on the first wavelength PPG signal and the second wavelength PPG signal.

2. The electronic fitness device of claim 1, wherein the optical signals transmitted from the first optical transmitter array to the first optical receiver travel a greater distance than the optical signals transmitted from the first optical transmitter array to the second optical receiver.

3. The electronic fitness device of claim 1, wherein the processing element is further configured to utilize the first wavelength PPG signal and the second wavelength PPG signal to determine a pulse oximetry of the user.

4. The electronic fitness device of claim 3, wherein the first wavelength ranges from approximately 630 nm to approximately 660 nm and the second wavelength ranges from approximately 900 nm to approximately 940 nm.

5. The electronic fitness device of claim 1, wherein the produced first wavelength PPG signal is an average of the first PPG signal and the third PPG signal.

6. The electronic fitness device of claim 1, wherein the produced second wavelength PPG signal is an average of the second PPG signal and the fourth PPG signal.

7. The electronic fitness device of claim 1, wherein the processing element is further configured to utilize the second wavelength PPG signal to minimize a motion component of the first wavelength PPG signal.

8. The electronic fitness device of claim 1, wherein the processing element is further configured to identify a component of the second PPG signal which is substantially correlated with one or more components of the fourth PPG signal and wherein the second wavelength PPG signal is produced based on the correlation of the second PPG signal and the fourth PPG signal.

9. The electronic fitness device of claim 1, wherein the processing element is further configured to utilize the first wavelength PPG signal to determine a heart rate of the user.

10. The electronic fitness device of claim 1, wherein the processing element is further configured to:
   produce a motion-compensated first PPG signal by reducing a motion component of the first PPG signal based on the second PPG signal,
   produce a motion-compensated third PPG signal by reducing a motion component of the third PPG signal based on the fourth PPG signal, and
   produce a first wavelength PPG signal based on the motion-compensated first PPG signal and the motion-compensated third PPG signal.

11. The electronic fitness device of claim 1, wherein the first optical transmitter array further includes a third optical transmitter configured to transmit a third optical signal having a third wavelength and a fourth optical transmitter configured to transmit a fourth optical signal having a fourth wavelength.

12. The electronic fitness device of claim 11, wherein the first wavelength ranges from approximately 540 nm to approximately 580 nm, the second wavelength ranges from approximately 660 nm to approximately 700 nm, the third wavelength ranges from approximately 630 nm to approximately 660 nm, and the fourth optical wavelength ranges from approximately 900 nm to approximately 940 nm.

13. The electronic fitness device of claim 11, further comprising:
- a second optical transmitter array positioned in a fourth opening on the bottom wall and including a fifth optical transmitter configured to transmit a fifth optical signal and a sixth optical transmitter configured to transmit a sixth optical signal; and
- a fourth lens covering the second optical transmitter array and configured to direct the fifth and sixth optical signals into the skin of the user,
- wherein the fifth optical signal has the first wavelength and the sixth optical signal has the second wavelength.

14. An electronic fitness device comprising:
- a housing including a bottom wall and one or more side walls;
- a first optical transmitter positioned along the bottom wall and configured to transmit a first optical signal having a first wavelength into the skin of a user;
- a second optical transmitter positioned along the bottom wall and configured to transmit a second optical signal having a second wavelength into the skin of the user;
- a first optical receiver positioned along the bottom wall, the first optical receiver configured to receive optical signals modulated by the skin of the user and generate a first photoplethysmogram (PPG) signal related to the first wavelength and a second PPG signal related to the second wavelength;
- a second optical receiver positioned along the bottom wall, the second optical receiver configured to receive optical signals modulated by the skin of the user and generate a third PPG signal related to the first wavelength and a fourth PPG signal related to the second wavelength; and
- a processing element in electronic communication with the optical transmitters and the optical receivers, the processing element configured to:
    - control each optical transmitter to transmit its optical signal during a separate period of time,
    - receive the PPG signals from the first optical receiver and the second optical receiver,
    - identify a component of the first PPG signal that is substantially correlated with one or more components of the third PPG signal,
    - produce a first wavelength PPG signal based on the correlation of the first PPG signal and the third PPG signal,
    - utilize the second PPG signal and the fourth PPG signal to produce a second wavelength PPG signal, and
    - determine cardiac information of the user based on the first and second wavelength PPG signals.

15. The electronic fitness device of claim 14, wherein the processing element is further configured to utilize the first wavelength PPG signal and the second wavelength PPG signal to determine a pulse oximetry of the user.

16. The electronic fitness device of claim 15, wherein the first wavelength ranges from approximately 630 nm to approximately 660 nm and the second wavelength ranges from approximately 900 nm to approximately 940 nm.

* * * * *